(12) United States Patent
Elzein et al.

(10) Patent No.: US 7,125,993 B2
(45) Date of Patent: *Oct. 24, 2006

(54) A$_{2B}$ ADENOSINE RECEPTOR ANTAGONISTS

(75) Inventors: Elfatih Elzein, Fremont, CA (US); Rao Kalla, Cupertino, CA (US); Tim Marquart, Mountain View, CA (US); Jeff Zablocki, Mountain View, CA (US); Xiaofen Li, Palo Alto, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 318 days.

This patent is subject to a terminal disclaimer.

(21) Appl. No.: 10/719,102

(22) Filed: Nov. 21, 2003

(65) Prior Publication Data

US 2004/0176399 A1   Sep. 9, 2004

Related U.S. Application Data

(63) Continuation-in-part of application No. 10/431,167, filed on May 6, 2003, now Pat. No. 6,977,300, which is a continuation-in-part of application No. 10/290,921, filed on Nov. 8, 2002, now Pat. No. 6,825,349.

(60) Provisional application No. 60/348,222, filed on Nov. 9, 2001.

(51) Int. Cl.
C07D 473/04 (2006.01)
C07D 473/06 (2006.01)
C07D 473/08 (2006.01)
C07D 247/02 (2006.01)
C07D 239/545 (2006.01)

(52) U.S. Cl. ............ 544/270; 544/267; 544/269; 544/271; 544/272; 544/310; 544/312

(58) Field of Classification Search ........ 544/267, 544/269, 270, 271, 272
See application file for complete search history.

(56) References Cited

U.S. PATENT DOCUMENTS

| | | | |
|---|---|---|---|
| 4,452,788 A | 6/1984 | Bristol et al. | |
| 4,558,051 A | 12/1985 | Sunshine et al. | |
| 4,593,095 A | 6/1986 | Snyder et al. | |
| 4,879,296 A | 11/1989 | Daluge et al. | |
| 5,446,046 A | * 8/1995 | Belardinelli et al. ... | 514/263.24 |
| 5,532,368 A | 7/1996 | Kufner-Muhl et al. | |
| 5,641,784 A | 6/1997 | Kufner-Muhl et al. | |
| 5,714,494 A | 2/1998 | Connell et al. | |
| 6,060,481 A | 5/2000 | La Noue et al. | |
| 6,117,878 A | 9/2000 | Linden | |
| 6,437,124 B1 | 8/2002 | Daluge et al. | |
| 6,545,002 B1 | 4/2003 | Linden et al. | |

FOREIGN PATENT DOCUMENTS

EP   0386683   9/1990

| EP | 956855 | 11/1999 |
|---|---|---|
| EP | 0956855 A | 11/1999 |
| EP | 1084710 | 3/2001 |
| WO | WO 9511681 | 5/1995 |
| WO | WO 9942093 | 8/1999 |
| WO | WO 0009507 | 2/2000 |
| WO | WO 0073307 | 12/2000 |

OTHER PUBLICATIONS

Jacobson K A et al: "1,3-Dialkylxanthine derivatives having high potency as antagonists at human A2B adenosine receptors", Drug Development Research, New York, NY, US, vol. 47, No. 1, 1999, pp. 45-53, XP000942540, abstract; example 10D.

(Continued)

*Primary Examiner*—Mark L. Berch
(74) *Attorney, Agent, or Firm*—Brian Lewis; J. Elin Hartru; CV Therapeutics, Inc.

(57) ABSTRACT

Disclosed are processes for the synthesis of novel compounds that are A$_{2B}$ adenosine receptor antagonists, having the structure of Formula I or Formula II:

Formula I

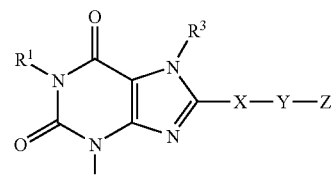

Formula II
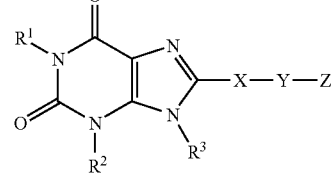

by cyclizing a compound of the formula (3):

(3)

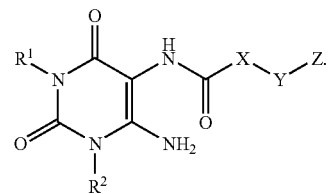

47 Claims, No Drawings

OTHER PUBLICATIONS

Kuz' Menko II et al, "Reactions of Theophyllines, Chemical Conversions of 8-Aminotheophyllinates" Chemistry of Heterocyclic Compounds (A translation of Khimiya Geterotsiklicheskikh Soedinenii), Plenum Press Co., New york NY, US, vol. 36, No. 8, 2000 pp. 963-970 XP001146936 ISSN: 0009-3122 examples 3K,3L,8.

* cited by examiner

$A_{2B}$ ADENOSINE RECEPTOR ANTAGONISTS

This is a Continuation in Part of U.S. Non-Provisional Patent Application Ser. No. 10/431,167, filed May 6, 2003, now U.S. Pat. No. 6,977,300, which is a Continuation in Part of U.S. Non-Provisional Patent Application Ser. No. 10/290,921, filed Nov. 8, 2002, now U.S. Pat. No. 6,825,349, which claims priority to U.S. Provisional Patent Application Ser. No. 60/348,222, filed Nov. 9, 2001, the complete disclosures of which are hereby incorporated by reference.

FIELD OF THE INVENTION

The present invention relates to $A_{2B}$ adenosine receptor antagonists, and to their use in treating mammals for various disease states, such as gastrointestinal disorders, immunological disorders, neurological disorders, and cardiovascular diseases due to both cellular hyperproliferation and apoptosis, and the like. The invention also relates to methods for the preparation of such compounds, and to pharmaceutical compositions containing them.

BACKGROUND

Adenosine is a naturally occurring nucleoside, which exerts its biological effects by interacting with a family of adenosine receptors characterized as $A_1$, $A_{2A}$, $A_{2B}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153), and $A_3$ adenosine receptors modulate cell proliferation processes.

Adenosine $A_{2B}$ receptors are ubiquitous, and regulate multiple biological activities. For example, adenosine binds to $A_{2B}$ receptors on endothelial cells, thereby stimulating angiogenesis. Adenosine also regulates the growth of smooth muscle cell populations in blood vessels. Adenosine stimulates $A_{2B}$ receptors on mast cells, thus modulating Type I hypersensitivity reactions. Adenosine also stimulates gastrosecretory activity by ligation with $A_{2B}$ in the intestine.

While many of these biological effects of adenosine are necessary to maintain normal tissue homeostasis, under certain physiological changes it is desirable to modulate its effects. For example, the binding of $A_{2B}$ receptors stimulates angiogenesis by promoting the growth of endothelial cells. Such activity is necessary in healing wounds, but the hyperproliferation of endothelial cells promotes diabetic retinopathy. Also, an undesirable increase in blood vessels occurs in neoplasia. Accordingly, inhibition of the binding of adenosine to $A_{2B}$ receptors in the endothelium will alleviate or prevent hypervasculation, thus preventing retinopathy and inhibiting tumor formation.

$A_{2B}$ receptors are found in the colon in the basolateral domains of intestinal epithelial cells, and when acted upon by the appropriate ligand act to increase chloride secretion, thus causing diarrhea, which is a common and potentially fatal complication of infectious diseases such as cholera and typhus. $A_{2B}$ antagonists can therefore be used to block intestinal chloride secretion, and are thus useful in the treatment of inflammatory gastrointestinal tract disorders, including diarrhea.

Insensitivity to insulin exacerbates diabetes and obesity. Insulin sensitivity is decreased by the interaction of adenosine with $A_{2B}$ receptors. Thus, blocking the adenosine $A_{2B}$ receptors of individuals with diabetes or obesity would benefit patients with these disorders. It has also been demonstrated that $A_{2B}$-antagonists cause a reduction of blood glucose levels, and thus would be particularly useful in the treatment of type-II diabetes.

Another adverse biological effect of adenosine acting at the $A_{2B}$ receptor is the over-stimulation of cerebral IL-6, a cytokine associated with dementias and Altheimer's disease. Inhibiting the binding of adenosine to $A_{2B}$ receptors would therefore mitigate those neurological disorders that are produced by IL-6.

Type I hypersensitivity disorders, such as asthma, hay fever, and atopic eczema, are stimulated by binding to $A_{2B}$-receptors of mast cells. Therefore, blocking these adenosine receptors would provide a therapeutic benefit against such disorders.

There are several compounds presently used in the treatment of asthma. For example, theophylline is an effective antiasthmatic agent, even though it is a poor adenosine receptor antagonist. However, considerable plasma levels are needed for it to be effective. Additionally, theophylline has substantial side effects, most of which are due to its CNS action, which provide no beneficial effects in asthma, and to the fact that it non-specifically blocks all adenosine receptor subtypes.

Additionally adenosine treatment, such as inhaled adenosine (or adenosine monophosphate), provokes bronchoconstriction in asthmatics, but not in the normal population. This process is known to involve mast cell activation, in that it releases mast cell mediators, including histamine, PGD2-β-hexosamimidase and tryptase, and because it can be blocked by specific histamine $H_1$ blockers and chromolyn sodium. Accordingly, there is an intrinsic difference in the way adenosine interacts with mast cells from asthmatics, and thus $A_{2B}$ antagonists are particularly useful in modulating mast cell function or in the activation of human lung cells.

Accordingly, it is desired to provide compounds that are potent $A_{2B}$ antagonists (i.e., compounds that inhibit the $A_{2B}$ adenosine receptor), fully or partially selective for the $A_{2B}$ receptor, useful in the treatment of various disease states related to modulation of the $A_{2B}$ receptor, for example cancer, asthma and diarrhea.

SUMMARY OF THE INVENTION

U.S. Non-Provisional Patent Application Ser. No. 10/431,167 discloses novel $A_{2B}$ adenosine receptor antagonists A category of preferred compounds that fall within the scope of this invention has been identified. Preferred compounds of Formula I include those in which $R^1$ and $R^2$ are independently optionally substituted lower alkyl, especially those compounds in which $R^1$ and $R^2$ are different, and are lower alkyl optionally substituted by cycloalkyl. More preferred are those compounds in which X is pyrazol-4-yl, Y is methylene, and Z is optionally substituted phenyl, especially phenyl substituted with trifluoromethyl. Even more preferred are those compounds in which $R^1$ and $R^2$ are chosen from ethyl, n-propyl cyclopropylmethyl, or iso-butyl, especially those in which $R^1$ is n-propyl and $R^2$ is ethyl. A preferred Z is 3-trifluoromethylphenyl. Consequently, novel processes for the preparation of such compounds have been developed.

Accordingly, in a first aspect, the invention relates to a process for the preparation of a compound of the formula:

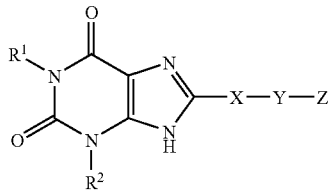

Formula I wherein:
R¹ and R² are independently optionally substituted alkyl;
X is optionally substituted arylene or optionally substituted heteroarylene;
Y is a covalent bond or lower alkylene; and
Z is optionally substituted monocyclic aryl or optionally substituted monocyclic heteroaryl;

comprising;

contacting a compound of the formula:

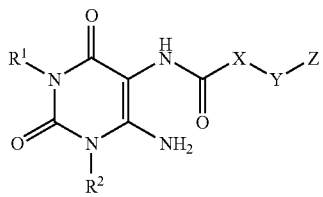

(3)

in which R¹, R², X, Y, and Z are as defined above;

with a base.

In a preferred embodiment, the compound of formula (3) is contacted with a base, preferably in a protic solvent. The base is preferably chosen from sodium hydroxide, potassium hydroxide, sodium methoxide, sodium ethoxide, and potassium t-butoxide preferably aqueous sodium hydroxide solution, and the protic solvent is preferably methanol.

In a second aspect, the invention relates to a process for the preparation of a compound of formula (3):

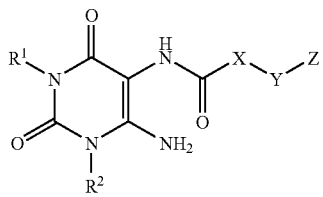

(3)

in which R¹, R², X, Y and Z are as defined above;

comprising:

contacting a compound of the formula (2);

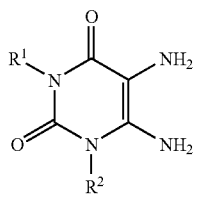

(2)

with a carboxylic acid of the formula Z-Y—X—CO₂H;

in which X, Y and Z are as defined above.

In a preferred embodiment, the compound of formula (2) is contacted with a compound of the formula Z-Y—X—CO₂H in a polar solvent, preferably methanol, in the presence of a coupling agent used to form amide bonds, preferably a carbodiimide derivative. In a more preferred embodiment the carbodiimide derivative is 1-(3-dimethylaminopropyl)-3-ethylcarbodiimide. Alternatively, the compound of formula (2) is contacted with an acid halide of the formula Z-Y—X—C(O)L, where L is chloro or bromo.

In a third aspect, the invention relates to a process for the preparation of a compound of formula (3):

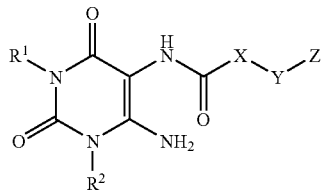

(3)

in which R¹, R², X, Y and Z are as defined above;

comprising:

contacting a compound of the formula (16);

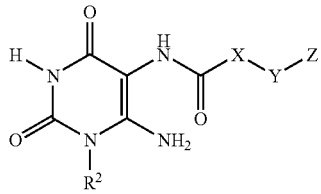

(16)

in which R², X, Y and Z are as defined above;

with a compound of the formula R¹L, in which L is a leaving group.

In a preferred embodiment, the compound of formula (16) is contacted with an alkyl halide, preferably an alkyl iodide, in the presence of a base, preferably potassium carbonate, in a polar solvent, preferably N,N-dimethylformamide.

In a fourth aspect, the invention relates to a process for the preparation of a compound of formula (3):

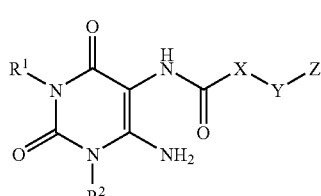

(3)

in which R¹, R², X, Y and Z are as defined above;

comprising:

contacting a compound of formula (13)

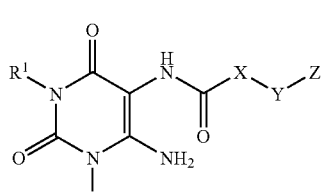

(13)

in which $R^1$, X, Y and Z are as defined above;

with a compound of the formula $R^2L$, in which L is a leaving group.

In a preferred embodiment, the compound of formula (13) is contacted with an alkyl halide, preferably an alkyl iodide, in the presence of a base, preferably potassium carbonate, in a polar solvent, preferably N,N-dimethylformamide.

In a fifth aspect, the invention relates to a process for the preparation of a compound of formula (16):

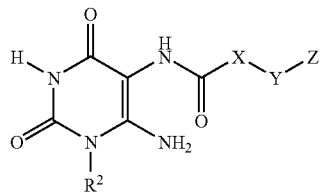
(16)

in which $R^2$, X, Y and Z are as defined above;

comprising:

contacting a compound of formula (15):

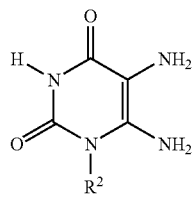
(15)

in which $R^2$ is as defined above;

with a carboxylic acid of the formula Z-Y—X—$CO_2H$;

in which X, Y and Z are as defined above.

In a preferred embodiment, the compound of formula (15) is contacted with a compound of the formula Z-Y—X—$CO_2H$ in a polar solvent, preferably methanol, in the presence of a coupling agent used to form amide bonds, preferably a carbodiimide derivative. In a more preferred embodiment the carbodiimide derivative is 1-(3-dimethylaminopropyl)-3-ethylcarbodiimide. Alternatively, the compound of formula (15) is contacted with an acid halide of the formula Z-Y—X—C(O)L, where L is chloro or bromo.

In a sixth aspect, the invention relates to a process for the preparation of a compound of formula (13):

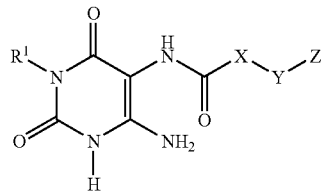
(13)

in which $R^1$, X, Y and Z are as defined above;

comprising:

contacting a compound of formula (12)

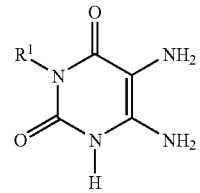
(12)

in which $R^1$ is as defined above;

with a carboxylic acid of the formula Z-Y—X—$CO_2H$;

in which X, Y and Z are as defined above.

In a preferred embodiment, the compound of formula (12) is contacted with a compound of the formula Z-Y—X—$CO_2H$ in a polar solvent, preferably methanol, in the presence of a coupling agent used to form amide bonds, preferably a carbodiimide derivative. In a more preferred embodiment the carbodiimide derivative is 1-(3-dimethylaminopropyl)-3-ethylcarbodiimide. Alternatively, the compound of formula (12) is contacted with an acid halide of the formula Z-Y—X—C(O)L, where L is chloro or bromo.

In a seventh aspect, the invention relates to a process for the preparation of a compound of formula (15):

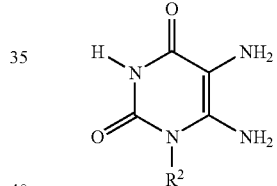
(15)

in which $R^2$ is as defined above;

comprising the steps of:

1) contacting a compound of formula (4):

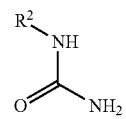
(4)

with ethyl cyanoacetate in the presence of a base in a protic solvent, preferably ethanol/sodium ethoxide;

2) contacting the product thus formed:

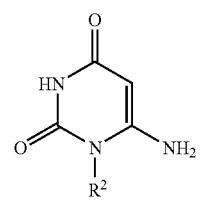
(5)

with a mixture of sodium nitrite in acetic acid/water; and 3) contacting the product thus formed:

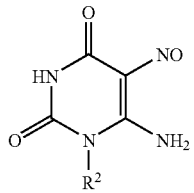
(14)

with a mixture of aqueous ammonia and sodium dithionite.

In an eighth aspect, the invention relates to a process for the preparation of a compound of formula (12):

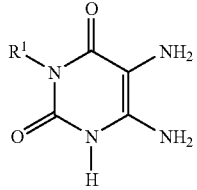
(12)

in which $R^1$ is as defined above;

comprising the steps of:
1) contacting a compound of the formula:

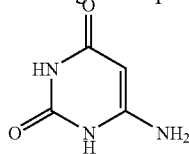

with a) hexamethyldisilazane followed by b) $R^1L$, where $R^1$ is as defined above and L is a leaving group;
2) contacting the compound thus formed:

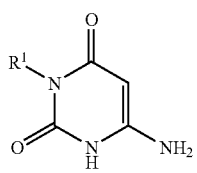
(10)

with a mixture of sodium nitrite in acetic acid/water; and
3) contacting the product thus formed:

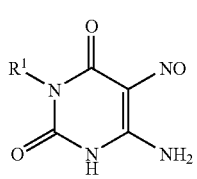
(11)

with a mixture of aqueous ammonia and sodium dithionite.

In a ninth aspect, the invention relates to a process for the preparation of a compound of formula (2):

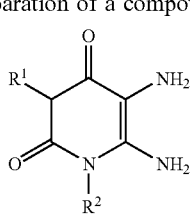
(2)

in which $R^1$ and $R^2$ are as defined above;

comprising the steps of:
1) contacting a compound of the formula:

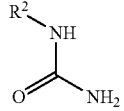
(4)

with ethyl cyanoacetate in the presence of a base in a protic solvent, preferably ethanol/sodium ethoxide;
2) contacting the product thus formed:

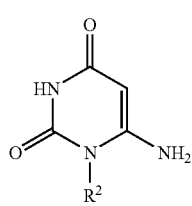
(5)

with the dimethylacetal of N,N-dimethylformamide;
3) contacting the product thus formed:

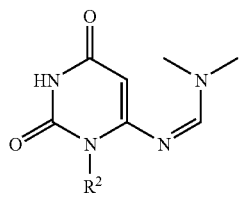
(6)

with a compound of formula $R^1L$, in which L is a leaving group, preferably an iodide, in the presence of a base, preferably potassium carbonate, in a polar solvent, preferably N,N-dimethylformamide.
4) contacting the product thus formed:

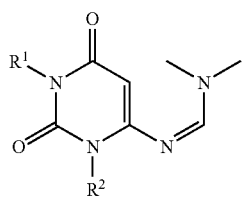
(7)

with aqueous ammonia;

5) contacting the product thus formed:

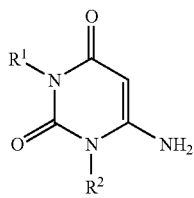

(8)

with a mixture of sodium nitrite in acetic acid/water; and
6) contacting the product thus formed:

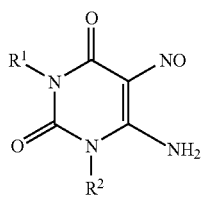

(1)

with a mixture of aqueous ammonia and sodium dithionite.

In a tenth aspect, the invention relates to a process for the preparation of a compound of formula (7)

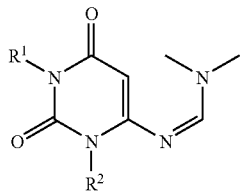

(7)

comprising the steps of:
1) contacting a compound of the formula:

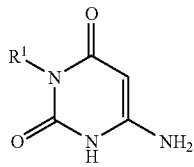

with the dimethylacetal of N,N-dimethylformamide;
2) contacting the product thus formed:

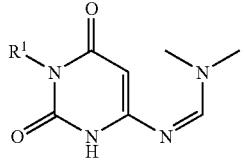

with a compound of formula $R^2L$, in which L is a leaving group, preferably an iodide, in the presence of a base, preferably potassium carbonate, in a polar solvent, preferably N,N-dimethylformamide; and
3) contacting the product thus formed:

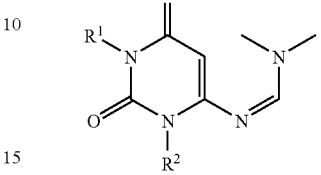

with aqueous ammonia.

In an eleventh aspect, the invention relates to a novel intermediate of the formula:

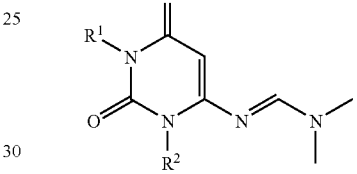

in which $R^1$ is n-propyl, 2-methylpropyl, or cyclopropylmethyl and $R^2$ is methyl or ethyl.

Particularly preferred is the compound in which $R^1$ is n-propyl and $R^2$ is ethyl:

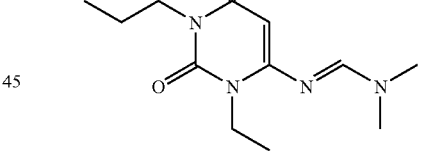

namely 6-[2-(dimethylamino)-1-azavinyl]-1-ethyl-3-propyl-1,3-dihydropyrimidine-2,4-dione.

In a twelfth aspect, the invention relates to a novel intermediate of the formula:

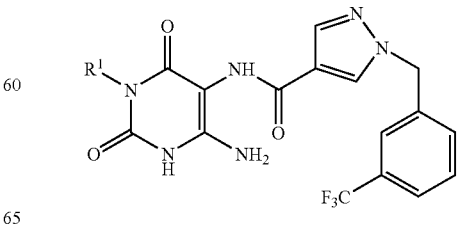

in which R¹ is n-propyl or cyclopropylmethyl, preferably n-propyl

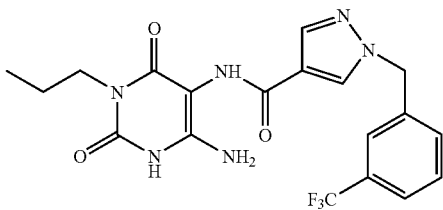

namely N-(6-amino-2,4-dioxo-3-propyl(1,3-dihydropyrimidin-5-yl))(1-{[3-(trifluoromethyl)-phenyl]methyl}pyrazol-4-yl)carboxamide.

In a thirteenth aspect, the invention relates to a novel intermediate of the formula:

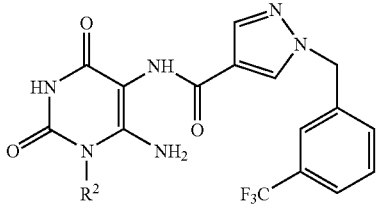

in which R² is methyl or ethyl, preferably ethyl;

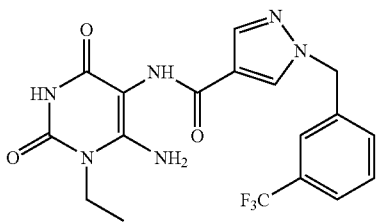

namely N-(6-amino-1-ethyl-2,4-dioxo(1,3-dihydropyrimidin-5-yl))(1-{[3-(trifluoromethyl)phenyl]methyl}pyrazol-4-yl)carboxamide;

In a fourteenth aspect, the invention relates to a novel intermediate of the formula:

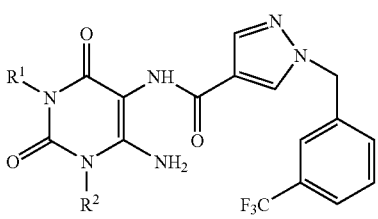

in which R¹ is n-propyl, 2-methylpropyl, or cyclopropylmethyl and R² is methyl or ethyl.

Particularly preferred is the intermediate in which R¹ is n-propyl and R² is ethyl;

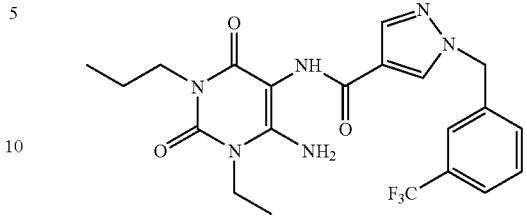

namely N-(6-amino-1-ethyl-2,4-dioxo-3-propyl(1,3-dihydropyrimidin-5-yl))(1-{[3-(trifluoromethyl)phenyl]methyl}pyrazol-4-yl)carboxamide.

Other aspects of the invention relates to pharmaceutical formulations, comprising a therapeutically effective amount of a compound of Formula I and at least one pharmaceutically acceptable excipient.

A further aspect of this invention relates to a method of using the compounds of Formula I in the treatment of a disease or condition in a mammal that is treatable by inhibiting an adenosine receptor characterized as $A_{2B}$, comprising administering to a mammal in need thereof a therapeutically effective dose of a compound of Formula I. Such diseases include, but are not limited to, at least one of asthma, inflammatory gastrointestinal tract disorders, including diarrhea, cardiovascular diseases such as atherosclerosis, neurological disorders such as senile dementia, Alzheimer's disease, and Parkinson's disease, and diseases related to angiogenesis, for example diabetic retinopathy and cancer.

One preferred group of compounds of Formula I are those in which R¹ and R² are different and are independently lower alkyl optionally substituted by cycloalkyl. Within this group, a first preferred class of compounds include those in which R¹ is lower alkyl of 2–4 carbon atoms optionally substituted by cyclopropyl and R² is lower alkyl of 2–4 carbon atoms, particularly where R¹ and R² are chosen from ethyl and n-propyl, and X is optionally substituted pyrazolen-1,4-yl. Within this class, a preferred subclass of compounds is where Y is lower alkylene, preferably methylene, and Z is optionally substituted phenyl, preferably 3-trifluoromethylphenyl. Most preferred are those compounds of Formula I in which R¹ is n-propyl and R² is ethyl.

At present, the preferred compounds are:
3-ethyl-1-propyl-8-(1-{[3-(trifluoromethyl)phenyl]methyl}pyrazol-4-yl)-1,3,7-trihydropurine-2,6-dione;
1-cyclopropylmethyl-3-methyl-8-[1-(phenylmethyl)pyrazol-4-yl]-1,3,7-trihydropurine-2,6-dione;
1-cyclopropylmethyl-3-methyl-8-{1-[(3-trifluoromethylphenyl)methyl]pyrazol-4-yl}-1,3,7-trihydropurine-2,6-dione;
1-cyclopropylmethyl-3-ethyl-8-{1-[(3-trifluoromethylphenyl)methyl]pyrazol-4-yl}-1,3,7-trihydropurine-2,6-dione;
1-cyclopropylmethyl-3-methyl-8-{1-[(3-fluorophenyl)methyl]pyrazol-4-yl}-1,3,7-trihydropurine-2,6-dione;
1-cyclopropylmethyl-3-ethyl-8-{1-[(3-fluorophenyl)methyl]pyrazol-4-yl}-1,3,7-trihydropurine-2,6-dione;
1-cyclopropylmethyl-3-ethyl-8-(1-{[6-(trifluoromethyl)(3-pyridyl)]methyl}pyrazol-4-yl)-1,3,7-trihydropurine-2,6-dione; 3-({4-[1-(cyclopropylmethyl)-3-methyl-2,6-dioxo-1,3,7-trihydropurin-8-yl]pyrazolyl}methyl)benzenecarbonitrile;

8-[1-(2-(1H-1,2,3,4-tetraazol-5-yl)ethyl)pyrazol-4-yl]-3-methyl-1-cyclopropylmethyl-1,3,7-trihydropurine-2,6-dione;

1-(2-methylpropyl)-3-methyl-8-[1-benzylpyrazol-4-yl]-1,3,7-trihydropurine-2,6-dione;

1-(2-methylpropyl)-3-ethyl-8-{1-[(3-fluorophenyl)methyl]pyrazol-4-yl}-1,3,7-trihydropurine-2,6-dione;

1-(2-methylpropyl)-3-methyl-8-{1-[(3-trifluoromethylphenyl)methyl]pyrazol-4-yl}-1,3,7-trihydropurine-2,6-dione;

1-(2-methylpropyl)-3-methyl-8-{1-[(3-fluorophenyl)methyl]pyrazol-4-yl}-1,3,7-trihydropurine-2,6-dione;

3-ethyl-1-(2-methylpropyl)-8-(1-{[6-(trifluoromethyl)(3-pyridyl)]methyl}pyrazol-4-yl)-1,3,7-trihydropurine-2,6-dione;

1-ethyl-3-methyl-8-{1-[(3-fluorophenyl)methyl]pyrazol-4-yl}-1,3,7-trihydropurine-2,6-dione; and 3-ethyl-1-propyl-8-[1-(2-pyridylmethyl)pyrazol-4-yl]-1,3,7-trihydropurine-2,6-dione.

Particularly preferred is 3-ethyl-1-propyl-8-(1-{[3-(trifluoromethyl)phenyl]-methyl}pyrazol-4-yl)-1,3,7-trihydropurine-2,6-dione.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1–10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1–10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1–10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1–20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—),1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy(or isobutoxy), n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl, Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —$S(O)_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

The term "heteroarylene" refers to a diradical of a heteroaryl group as defined above. This term is exemplified by groups such as 2,5-imidazolene, 3,5-[1,2,4]oxadiazolene, 2,4-oxazolene, 1,4-pyrazolene, and the like. For example, 1,4-pyrazolene is:

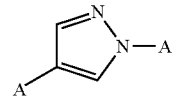

where A represents the point of attachment.

Unless otherwise constrained by the definition for the heteroaryl or heteroarylene substituent, such heteroaryl or heterarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2$R, in which R is alkyl, aryl, or heteroaryl. "Substituted sulfone" refers to a group —$S(O)_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

The term "coupling agent used to form amide bonds" refers to those compounds that are conventionally employed to facilitate formation of amide bonds through the reaction of a carboxylic acid and an amine. Examples of such coupling agents are 1-(3-dimethylaminopropyl)-3-ethylcarbodiimide, 1,3-di-t-butylcarbodiimide, 1,3-dicyclohexylcarbodiimide, and the like.

The term "leaving group" is used in the conventional manner, and refers to a moiety that is capable of being displaced by a nucleophile in a replacement or substitution reaction. Examples of leaving groups are chloro, bromo, iodo, mesylate, tosylate, and the like.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms;

and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is n-propyl, $R^2$ is ethyl, X is 1,4-pyrazolenyl, Y is —$CH_2$—, and Z is 3-trifluoromethylphenyl);

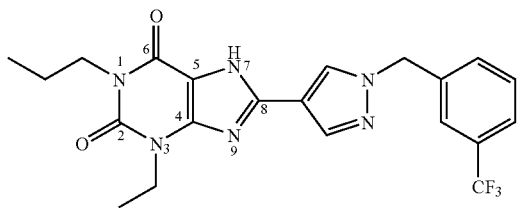

which is named:
3-ethyl-1-propyl-8-(1-{[3-(trifluoromethyl)phenyl]methyl}pyrazol-4-yl)-1,3,7-trihydropurine-2,6-dione.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Preparation of a Compound of Formula I

One preferred method of preparing compounds of Formula I is shown in Reaction Scheme I.

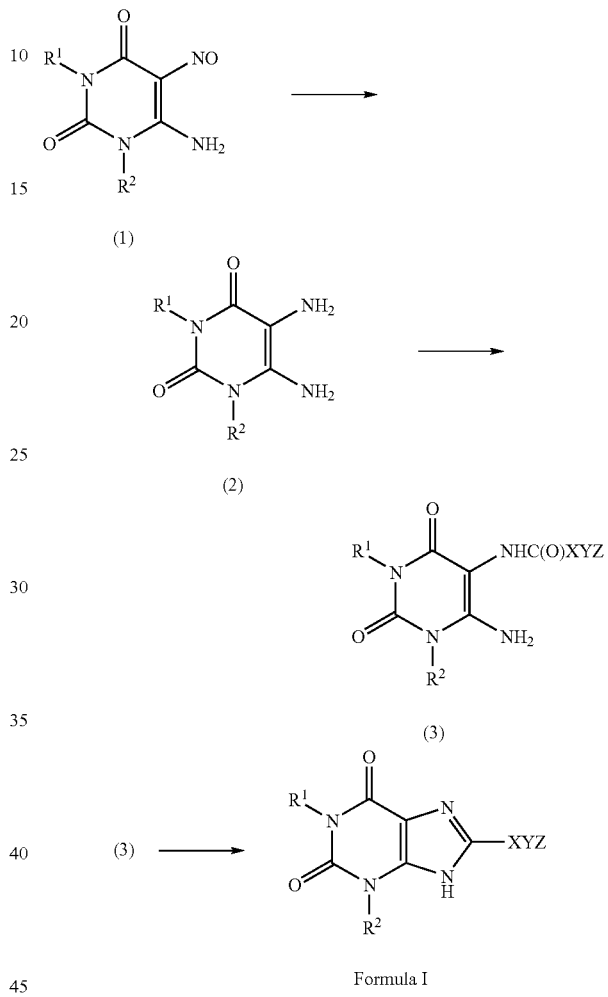

Step 1—Preparation of Formula (2)

The compound of formula (2) is made from the compound of formula (1) by a reduction step. Conventional reducing techniques may be used, for example using sodium dithionite in aqueous ammonia solution; preferably reduction is carried out with hydrogen and a metal catalyst. The reaction is carried out at in an inert solvent, for example methanol, in the presence of a catalyst, for example 10% palladium on carbon catalyst, under an atmosphere of hydrogen, preferably under pressure, for example at about 30 psi, for about 2 hours. When the reaction is substantially complete, the product of formula (2) is isolated by conventional means tp provide a compound of formula (2).

Step 2—Preparation of Formula (3)

The compound of formula (2) is then reacted with a carboxylic acid of the formula Z-Y—X—$CO_2H$ in the presence of a carbodiimide, for example 1-(3-dimethylaminopropyl)-3-ethylcarbodiimide hydrochloride. The reaction is conducted in a protic solvent, for example methanol, ethanol, propanol, and the like, preferably methanol, at a temperature of about 20–30° C., preferably about room temperature, for about 12–48 hours, preferably about 16 hours. When the reaction is substantially complete, the product of formula (3) is isolated conventionally, for example by removal of the solvent under reduced pressure, and washing the product. Alternatively, the next step can be carried out without any further purification.

Alternative Preparation of a Compound of Formula (3)

Alternatively, the carboxylic acid of the formula Z-Y—X—CO$_2$H is first converted to an acid halide of the formula Z-Y—X—C(O)L, where L is chloro or bromo, by reacting with a halogenating agent, for example thionyl chloride or thionyl bromide, preferably thiony chloride. Alternatively, oxalyl chloride, phosphorus pentachloride or phosphorus oxychloride may be used. The reaction is preferably conducted in the absence of a solvent, using excess halogenating agent, for example at a temperature of about 60–80° C., preferably about 70° C., for about 1–8 hours, preferably about 4 hours. When the reaction is substantially complete, the product of formula Z-Y—X—C(O)L is isolated conventionally, for example by removal of the excess halogenating agent under reduced pressure.

The product is then reacted with a compound of formula (2) in an inert solvent, for example acetonitrile, in the presence of a tertiary base, for example triethylamine. The reaction is conducted at an initial temperature of about 0C, and then allowed to warm to 20–30° C., preferably about room temperature, for about 12–48 hours, preferably about 16 hours. When the reaction is substantially complete, the product of formula (3) is isolated conventionally, for example by diluting the reaction mixture with water, filtering off the product, and washing the product with water followed by ether.

Step 3—Preparation of Formula I

The compound of formula (3) is then converted into a compound of Formula I by a cyclization reaction. The reaction is conducted in a protic solvent, for example methanol, ethanol, propanol, and the like, preferably methanol, in the presence of a base, for example potassium hydroxide, sodium hydroxide, sodium methoxide, sodium ethoxide, potassium t-butoxide, preferably aqueous sodium hydroxide, at a temperature of about 50–80° C., preferably about 80° C., for about 1–8 hours, preferably about 3 hours. When the reaction is substantially complete, the product of Formula I is isolated conventionally, for example by removal of the solvent under reduced pressure, acidifying the residue with an aqueous acid, filtering off the product, then washing and drying the product.

The compound of formula (1) may be prepared by various methods. One preferred method is shown in Reaction Scheme II.

REACTION SCHEME II

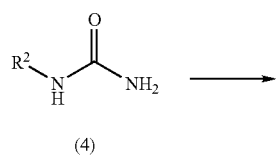

(4)

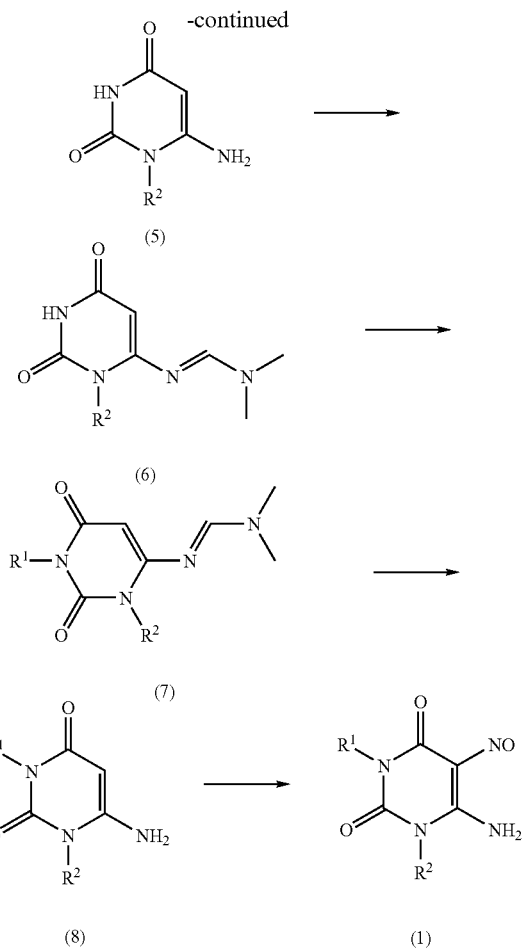

Step 1—Preparation of Formula (5)

The compound of formula (4) is either commercially available or prepared by means well known in the art. It is reacted with ethyl cyanoacetate in a protic solvent, for example ethanol, in the presence of a strong base, for example sodium ethoxide. The reaction is carried out at about reflux temperature, for about 4 to about 24 hours. When the reaction is substantially complete, the compound of formula (5) thus produced is isolated conventionally.

Step 2 and 3—Preparation of Formula (7)

The compound of formula (5) is reacted with the dimethylacetal of N,N-dimethylformamide in a polar solvent, for example N,N-dimethylformamide. The reaction is carried out at about 40° C., for about 1 hour. When the reaction is substantially complete, the compound of formula (6) thus produced is reacted with a compound of formula R$^1$Hal, where Hal is chloro, bromo, or iodo, in the presence of a base, for example potassium carbonate. The reaction is carried out at about 80° C., for about 4–24 hour. When the reaction is substantially complete, the product of formula (7) is isolated conventionally, for example by evaporation of the solvents under reduced pressure, and the residue is used in the next reaction with no further purification.

Step 4—Preparation of Formula (8)

The compound of formula (7) is reacted with aqueous ammonia in a polar solvent, for example suspended in methanol. The reaction is carried out at about room temperature, for about 1–3 days. When the reaction is substantially complete, the product of formula (8) is isolated conventionally, for example by chromatography over a silica gel column, eluting, for example, with a mixture of dichloromethane/methanol.

Step 5—Preparation of Formula (1)

The compound of formula (8) is then mixed with sodium nitrite in an aqueous acidic solvent, preferably acetic acid and water, for example 50% acetic acid/water. The reaction is carried out at a temperature of about 50–90° C., preferably about 70° C., for about 1 hour. When the reaction is substantially complete, the product of formula (1) is isolated by conventional means.

Alternatively, the reaction may be conducted in an aqueous solvent, for example dimethylformamide and water, and reacted with a strong acid, for example hydrochloric acid.

A compound of formula (8) can be prepared from a compound of formula (10) using a similar method, as shown in Reaction Scheme IIA.

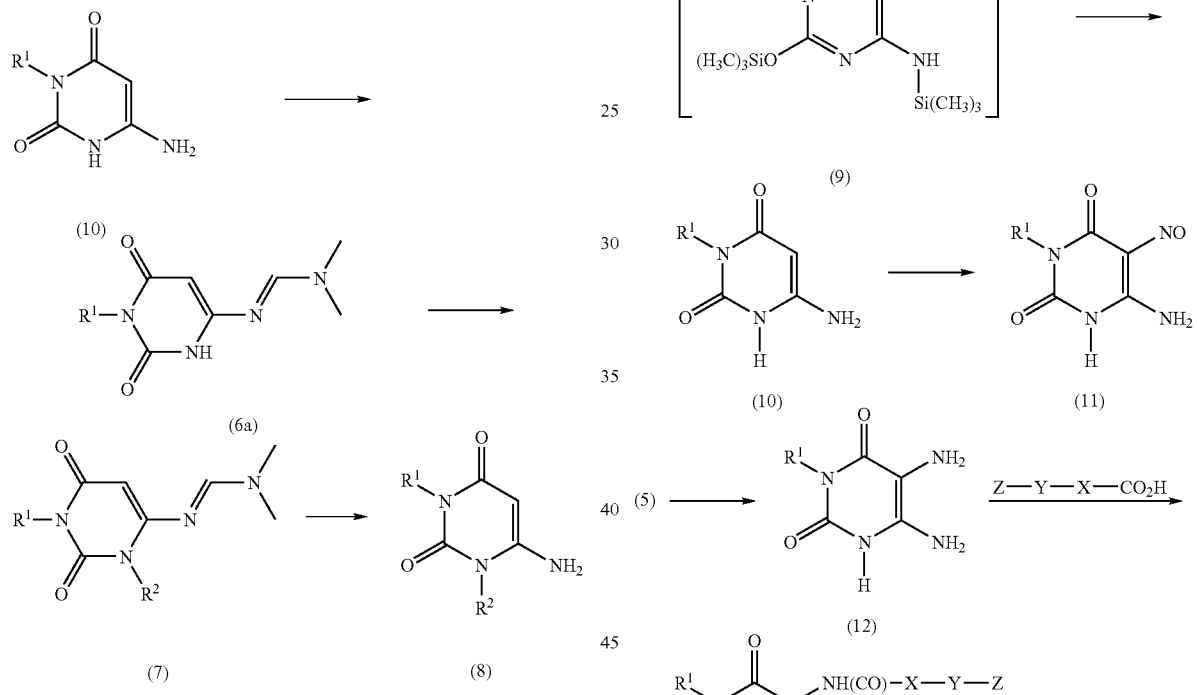

Step 2 and 3—Preparation of Formula (7)

The compound of formula (10) is reacted with the dimethylacetal of N,N-dimethylformamide in a polar solvent, for example N,N-dimethylformamide. The reaction is carried out at about 40° C., for about 1 hour. When the reaction is substantially complete, the compound of formula (6a) thus produced is reacted with a compound of formula $R^2Hal$, where Hal is chloro, bromo, or iodo, in the presence of a base, for example potassium carbonate. The reaction is carried out at about 80° C., for about 4–24 hour. When the reaction is substantially complete, the product of formula (7) is isolated conventionally, for example by evaporation of the solvents under reduced pressure, and the residue is used in the next reaction with no further purification.

Step 4—Preparation of Formula (8)

The compound of formula (7) is reacted with aqueous ammonia in a polar solvent, for example suspended in methanol. The reaction is carried out at about room temperature, for about 1–3 days. When the reaction is substantially complete, the product of formula (8) is isolated conventionally, for example by chromatography over a silica gel column, eluting, for example, with a mixture of dichloromethane/methanol.

The compound of formula (3) may also be prepared by various methods. One preferred method is shown in Reaction Scheme III.

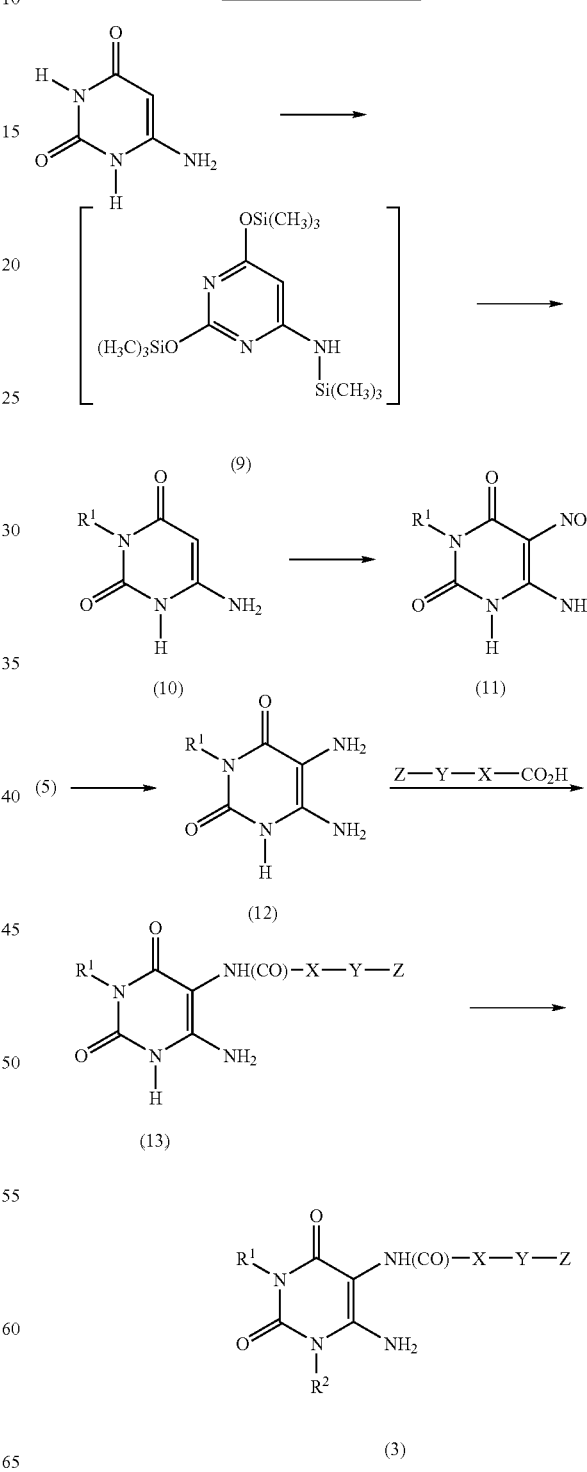

Step 1—Preparation of Formula (10)

The commercially available compound 6-aminouracil is first silylated, for example by reaction with excess hexamethyldisilazane as a solvent in the presence of a catalyst, for example ammonium sulfate. The reaction is carried out at about reflux temperature, for about 1–10 hours. When the reaction is substantially complete, the silylated compound thus produced is isolated conventionally, and then reacted with a compound of formula $R^1Hal$, where Hal is chloro, bromo, or iodo, preferably in the absence of a solvent. The reaction is carried out at about reflux, for about 4–48 hours, preferably about 12–16 hours. When the reaction is substantially complete, the product of formula (10) is isolated by conventional means.

Step 2—Preparation of Formula (11)

The compound of formula (10) is then dissolved in an aqueous acid, for example aqueous acetic acid, and reacted with sodium nitrite. The reaction is carried out at a temperature of about 20–50° C., preferably about 30° C., over about 30 minutes. When the reaction is substantially complete, the product of formula (11) is isolated by conventional means, for example by filtration.

Step 3—Preparation of Formula (12)

The compound of formula (11) is then reduced to a diamino derivative. In general, the compound of formula (11) is dissolved in aqueous ammonia, and then a reducing agent, for example sodium hydrosulfite, added. The reaction is conducted at a temperature of about 70° C. When the reaction is substantially complete, the product of formula (12) is isolated conventionally, for example by filtration of the cooled reaction mixture.

Step 4—Preparation of Formula (13)

The compound of formula (12) is then reacted with a carboxylic acid of the formula Z-Y—X—$CO_2H$ in the presence of a carbodiimide, for example 1-(3-dimethylaminopropyl)-3-ethylcarbodiimide hydrochloride. The reaction is conducted at a temperature of about 20–30° C., for about 12–48 hours. When the reaction is substantially complete, the product of formula (13) is isolated conventionally, for example by filtration of the cooled reaction mixture.

Alternatively, the carboxylic acid of the formula Z-Y—X—$CO_2H$ is converted to an acid halide of the formula Z-Y—X—C(O)L, where L is chloro or bromo, by reacting with a halogenating agent, for example thionyl chloride or thionyl bromide; alternatively, phosphorus pentachloride or phosphorus oxychloride may be used. The reaction is preferably conducted in the absence of a solvent, using excess halogenating agent, for example at a temperature of about 60–80° C., preferably about 70° C., for about 1–8 hours, preferably about 4 hours. When the reaction is substantially complete, the product of formula Z-Y—X—C(O)L is isolated conventionally, for example by removal of the excess halogenating agent under reduced pressure.

The product of the formula Z-Y—X—C(O)L is then reacted with a compound of formula (12) in an inert solvent, for example acetonitrile, in the presence of a tertiary base, for example triethylamine. The reaction is conducted at an initial temperature of about 0C, and then allowed to warm to 20–30° C., preferably about room temperature, for about 12–48 hours, preferably about 16 hours. When the reaction is substantially complete, the product of formula (13) is isolated conventionally, for example by diluting the reaction mixture with water, filtering off the product, and washing the product with water followed by ether.

Step 5—Preparation of Formula (3)

The compound of formula (13) is reacted with a compound of formula $R^2Hal$, where Hal is chloro, bromo, or iodo, in the presence of a base, for example potassium carbonate. The reaction is carried out at about room temperature, for about 4–24 hour, preferably about 16 hours. When the reaction is substantially complete, the product of formula (3) is isolated conventionally, for example by evaporation of the solvents under reduced pressure, and the residue may be purified conventionally, or may be used in the next reaction with no further purification.

Another method of preparing a compound of formula (3) is shown in Reaction Scheme IV.

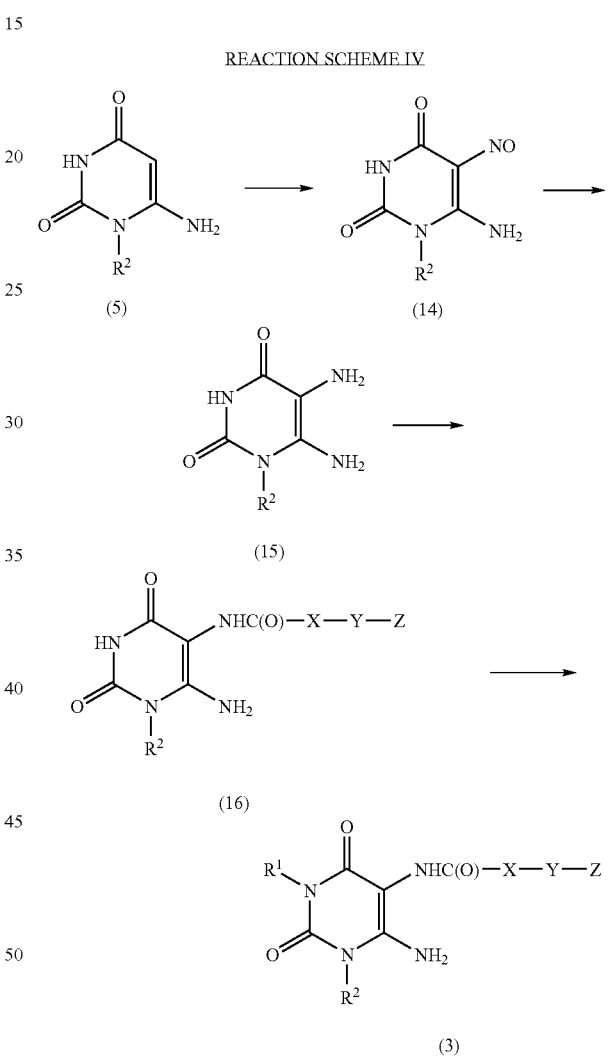

REACTION SCHEME IV

Step 1—Preparation on Formula (14)

The compound of formula (5) is then mixed with sodium nitrite in an aqueous acidic solvent, preferably acetic acid and water, for example 50% acetic acid/water. The reaction is carried out at a temperature of about 50–90° C., preferably about 70° C., for about 1 hour. When the reaction is substantially complete, the product of formula (14) is isolated by conventional means.

Alternatively, the reaction may be conducted in an aqueous solvent, for example dimethylformamide and water, and reacted with a strong acid, for example hydrochloric acid.

Step 3—Preparation of Formula (15)

The compound of formula (14) is then reduced to a diamino derivative. In general, the compound of formula (14) is dissolved in aqueous ammonia, and then a reducing agent, for example sodium hydrosulfite, added. The reaction is conducted at a temperature of about 70° C. When the reaction is substantially complete, the product of formula (15) is isolated conventionally, for example by filtration of the cooled reaction mixture.

Step 4—Preparation of Formula (16)

The compound of formula (15) is then reacted with a carboxylic acid of the formula Z-Y—X—CO$_2$H in the presence of a carbodiimide, for example 1-(3-dimethylaminopropyl)-3-ethylcarbodiimide hydrochloride. The reaction is conducted at a temperature of about 20–30° C., for about 12–48 hours, in an inert solvent, for example methanol. When the reaction is substantially complete, the product of formula (16) is isolated conventionally, for example by filtration of the cooled reaction mixture.

Alternatively, the carboxylic acid of the formula Z-Y—X—CO$_2$H is converted to an acid halide of the formula Z-Y—X—C(O)L, where L is chloro or bromo, by reacting with a halogenating agent, for example thionyl chloride or thionyl bromide; alternatively, phosphorus pentachloride or phosphorus oxychloride may be used. The reaction is preferably conducted in the absence of a solvent, using excess halogenating agent, for example at a temperature of about 60–80° C., preferably about 70° C., for about 1–8 hours, preferably about 4 hours. When the reaction is substantially complete, the product of formula Z-Y—X—C(O)L is isolated conventionally, for example by removal of the excess halogenating agent under reduced pressure.

The product of the formula Z-Y—X—C(O)L is then reacted with a compound of formula (15) in an inert solvent, for example acetonitrile, in the presence of a tertiary base, for example triethylamine. The reaction is conducted at an initial temperature of about 0C, and then allowed to warm to 20–30° C., preferably about room temperature, for about 12–48 hours, preferably about 16 hours. When the reaction is substantially complete, the product of formula (16) is isolated conventionally, for example by diluting the reaction mixture with water, filtering off the product, and washing the product with water followed by ether.

Step 5—Preparation of Formula (3)4

The compound of formula (16) is reacted with a compound of formula R$^1$Hal, where Hal is chloro, bromo, or iodo, in the presence of a base, for example potassium carbonate. The reaction is carried out at about 80° C., for about 4–24 hour, preferably about 16 hours. When the reaction is substantially complete, the product of formula (3) is isolated conventionally, for example by evaporation of the solvents under reduced pressure, and the residue may be purified conventionally, or may be used in the next reaction with no further purification.

An example of a synthesis of a compound of Z-Y—X—CO$_2$H in which X is pyrazol-1,4-yl, Y is methylene, and Z is 3-trifluoromethylphenyl, is shown in Reaction Scheme V.

REACTION SCHEME V

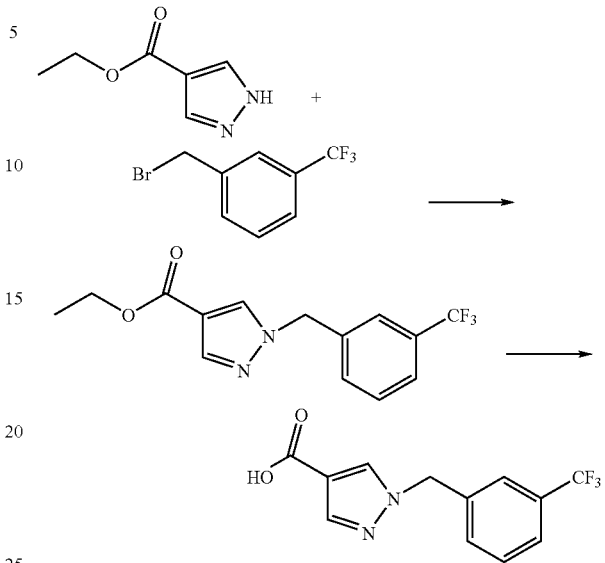

Ethyl pyrazole-4-carboxylate is reacted with 1-(bromomethyl)-3-(trifluoromethyl)benzene in acetone in the presence of potassium carbonate. The product, ethyl 1-{[3-(trifluoromethyl)phenyl]methyl}pyrazole-4-carboxylate, is then hydrolyzed with potassium hydroxide in methanol, to provide 1-{[3-(trifluoromethyl)phenyl]methyl}pyrazole-4-carboxylic acid.

Utility, Testing and Administration

General Utility

The compounds of Formula I are effective in the treatment of conditions that respond to administration of A$_{2B}$ adenosine receptor antagonists. Such conditions include, but are not limited to, at least one of diarrhea, atherosclerosis, restenosis, rheumatoid arthritis, diabetes, in particular type-II diabetes, macular degeneration, diabetic retinopathy, cancer, senile dementia, Alzheimer's disease, Parkinson's disease, traumatic brain injury, and Type I hypersensitivity reactions, including asthma, atopic eczema, and hay fever.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents.

Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modem Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (5)

A. Preparation of a Compound of Formula (5) in which $R^2$ is Ethyl

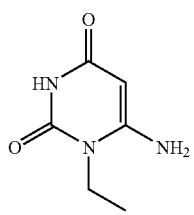

A solution of sodium ethoxide was prepared from sodium (4.8 g, 226 mmol) and dry ethanol (150 ml). To this solution was added amino-N-ethylamide (10 g, 113 mmol) and ethyl cyanoacetate (12.8 g, 113 mmol). This reaction mixture was stirred at reflux for 6 hours, cooled, and solvent removed from the reaction mixture under reduced pressure. The residue was dissolved in water (50 ml), and the pH adjusted to 7 with hydrochloric acid. The mixture was allowed to stand overnight at 0° C., and the precipitate filtered off, washed with water and air-dried, to provide 6-amino-1-ethyl-1,3-dihydropyrimidine-2,4-dione, a compound of formula (5).

$^1$H-NMR (DMSO-d6) δ 10.29 (s, 1H), 6.79 (s, 2H), 4.51 (s, 1H), 3.74–3.79 (m, 2H), 1.07 (t, 3H, J=7.03 Hz); MS m/z 155.98 (M$^+$), 177.99 (M$^+$+Na)

B. Preparation of a Compound of Formula (5) in which $R^2$ is Methyl

Similarly, following the procedure of Example 1A, but replacing amino-N-ethylamide with amino-N-methylamide, 6-amino-1-methyl-1,3-dihydropyrimidine-2,4-dione was prepared.

C. Preparation of a Compound of Formula (5) varying $R^2$

Similarly, following the procedure of Example 1A, but replacing amino-N-ethylamide with other compounds of formula (4), other compounds of formula (5) are prepared.

EXAMPLE 2

Preparation of a Compound of Formula (6)

A. Preparation of a Compound of Formula (6) in which $R^2$ is Ethyl

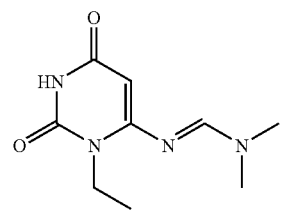

A suspension of 6-amino-1-ethyl-1,3-dihydropyrimidine-2,4-dione (0.77 g, 5 mmol) in anhydrous N,N-dimethylacetamide (25 ml) and N,N-dimethylformamide dimethylacetal (2.7 ml, 20 mmol) and was warmed at 40° C. for 90 minutes. Solvent was then removed under reduced pressure, and the residue triturated with ethanol, filtered, and washed with ethanol, to provide 6-[2-(dimethylamino)-1-azavinyl]-1-ethyl-1,3-dihydropyrimidine-2,4-dione, a compound of formula (6). $^1$H-NMR (DMSO-d6) δ 10.62 (s, 1H), 8.08 (s, 1H), 4.99 (s, 1H), 3.88–3.95 (m, 2H), 3.13 (s, 3H), 2.99 (s, 3H), 1.07 (t, 3H, J=7.03 Hz); MS m/z 210.86 (M$^+$), 232.87 (M$^+$+Na)

B. Preparation of a Compound of Formula (6) in which $R^2$ is Methyl

Similarly, following the procedure of Example 2A, but replacing 6-amino-1-ethyl-1,3-dihydropyrimidine-2,4-dione with 6-amino-1-methyl-1,3-dihydropyrimidine-2,4-dione, 6-[2-(dimethylamino)-1-azavinyl]-1-methyl-1,3-dihydropyrimidine-2,4-dione was prepared.

C. Preparation of a Compound of Formula (6) varying $R^2$

Similarly, following the procedure of Example 2A, but replacing 6-amino-1-ethyl-1,3-dihydropyrimidine-2,4-dione with other compounds of formula (5), other compounds of formula (6) are prepared.

EXAMPLE 3

Preparation of a Compound of Formula (7)

A. Preparation of a Compound of Formula (7) in which $R^1$ is n-Propyl and $R^2$ is Ethyl

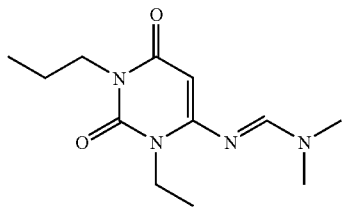

A mixture of a solution of 6-[2-(dimethylamino)-1-azavinyl]-1-ethyl-1,3-dihydropyrimidine-2,4-dione (1.5 g, 7.1 mmol) in dimethylformamide (25 ml), potassium carbonate (1.5 g, 11 mmol) and n-propyl iodide (1.54 g, 11 mmol) was stirred at 80° C. for 5 hours. The reaction mixture was cooled to room temperature, filtered, the solvents were evaporated and the product of formula (7), 6-[2-(dimethylamino)-1-azavinyl]-1-ethyl-3-propyl-1,3-dihydropyrimidine-2,4-dione, was used as such in the next reaction.

B. Preparation of a Compound of Formula (7) varying $R^1$ and $R^2$

Similarly, following the procedure of Example 3A, but replacing 6-[2-(dimethylamino)-1-azavinyl]-1-ethyl-1,3-dihydropyrimidine-2,4-dione with other compounds of formula (6), the following compounds of formula (7) were prepared:
6-[2-(dimethylamino)-1-azavinyl]-1-methyl-3-propyl-1,3-dihydropyrimidine-2,4-dione.
6-[2-(dimethylamino)-1-azavinyl]-1-methyl-3-cyclopropylmethyl-1,3-dihydropyrimidine-2,4-dione;
6-[2-(dimethylamino)-1-azavinyl]-1-ethyl-3-cyclopropylmethyl-1,3-dihydropyrimidine-2,4-dione;
6-[2-(dimethylamino)-1-azavinyl]-1-methyl-3-(2-methylpropyl)-1,3-dihydropyrimidine-2,4-dione; and
6-[2-(dimethylamino)-1-azavinyl]-1-ethyl-3-(2-methylpropyl)-1,3-dihydropyrimidine-2,4-dione.

C. Preparation of a Compound of Formula (7), varying $R^1$ and $R^2$

Similarly, following the procedure of Example 3A, but replacing 6-[2-(dimethylamino)-1-azavinyl]-1-ethyl-1,3-dihydropyrimidine-2,4-dione with other compounds of formula (6), other compounds of formula (7) are prepared.

EXAMPLE 4

Preparation of a Compound of Formula (8)

A. Preparation of a Compound of Formula (8) in which $R^1$ is n-Propyl and $R^2$ is Ethyl

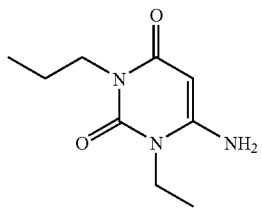

A solution of 6-[2-(dimethylamino)-1-azavinyl]-1-ethyl-3-propyl-1,3-dihydropyrimidine-2,4-dione (2.1 g) was dissolved in a mixture of methanol (10 ml) and 28% aqueous ammonia solution (20 ml), and stirred for 72 hours at room temperature. Solvent was then removed under reduced pressure, and the residue purified by chromatography on a silica gel column, eluting with a mixture of dichloromethane/methanol (15/1), to provide 6-amino-1-ethyl-3-propyl-1,3-dihydropyrimidine-2,4-dione, a compound of formula (8).

$^1$H-NMR (DMSO-d6) δ 6.80 (s, 2H), 4.64 (s, 1H), 3.79–3.84 (m, 2H), 3.63–3.67 (m, 2H), 1.41–1.51 (m, 2H), 1.09 (t, 3H, J=7.03 Hz), 0.80 (t, 3H, J=7.42 Hz); MS m/z 197.82 (M$^+$)

B. Preparation of a Compound of Formula (8), varying $R^1$ and $R^2$

Similarly, following the procedure of Example 4A, but replacing 6-[2-(dimethylamino)-1-azavinyl]-1-ethyl-3-propyl-1,3-dihydropyrimidine-2,4-dione with other compounds of formula (7), the following compounds of formula (8) were prepared:
6-amino-1-methyl-3-propyl-1,3-dihydropyrimidine-2,4-dione;
6-amino-1-methyl-3-cyclopropylmethyl-1,3-dihydropyrimidine-2,4-dione;
6-amino-1-ethyl-3-cyclopropylmethyl-1,3-dihydropyrimidine-2,4-dione;
6-amino-1-methyl-3-(2-methylpropyl)-1,3-dihydropyrimidine-2,4-dione; and
6-amino-1-ethyl-3-(2-methylpropyl)-1,3-dihydropyrimidine-2,4-dione.

C. Preparation of a Compound of Formula (7) varying $R^1$ and $R^2$

Similarly, following the procedure of Example 4A, but replacing 6-[2-(dimethylamino)-1-azavinyl]-1-ethyl-3-propyl-1,3-dihydropyrimidine-2,4-dione with other compounds of formula (7), other compounds of formula (8) are prepared.

EXAMPLE 5

Preparation of a Compound of Formula (1)

A. Preparation of a Compound of Formula (1) in which $R^1$ is n-Propyl and $R^2$ is Ethyl

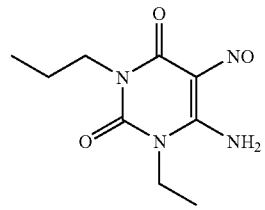

To a solution of 6-amino-1-ethyl-3-propyl-1,3-dihydropyrimidine-2,4-dione (1.4 g, 7.1 mmol) in a mixture of 50% acetic acid/water (35 ml) was added sodium nitrite (2 g, 28.4 mmol) in portions over a period of 10 minutes. The mixture was stirred at 70° C. for 1 hour, then the reaction mixture concentrated to a low volume under reduced pressure. The solid was filtered off, and washed with water, to provide 6-amino-1-ethyl-5-nitroso-3-propyl-1,3-dihydropyrimidine-2,4-dione, a compound of formula (1). MS m/z 227.05 (M$^+$), 249.08 (M$^+$+Na)

B. Preparation of a Compound of Formula (1), varying $R^1$ and $R^2$

Similarly, following the procedure of Example 5A, but replacing 6-amino-1-ethyl-3-propyl-1,3-dihydropyrimidine-2,4-dione with other compounds of formula (8), the following compounds of formula (1) were prepared:

6-amino-1-methyl-5-nitroso-3-propyl-1,3-dihydropyrimidine-2,4-dione;

6-amino-1-methyl-3-cyclopropylmethyl-5-nitroso-1,3-dihydropyrimidine-2,4-dione;

6-amino-1-ethyl-3-cyclopropylmethyl-5-nitroso-1,3-dihydropyrimidine-2,4-dione;

6-amino-1-methyl-3-(2-methylpropyl)-5-nitroso-1,3-dihydropyrimidine-2,4-dione; and 6-amino-1-ethyl-3-(2-methylpropyl)-5-nitroso-1,3-dihydropyrimidine-2,4-dione.

C. Preparation of a Compound of Formula (1) varying $R^1$ and $R^2$

Similarly, following the procedure of Example 5A, but replacing 6-amino-1-ethyl-3-propyl-1,3-dihydropyrimidine-2,4-dione with other compounds of formula (8), other compounds of formula (1) are prepared.

EXAMPLE 6

Preparation of a Compound of Formula (2)

A. Preparation of a Compound of Formula (2) in which $R^1$ is n-Propyl and $R^2$ is Ethyl

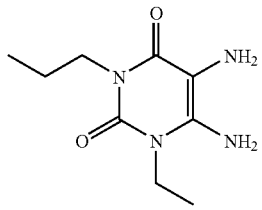

To a solution of 6-amino-1-ethyl-5-nitroso-3-propyl-1,3-dihydropyrimidine-2,4-dione (300 mg) in methanol (10 ml) was added 10% palladium on carbon catalyst (50 mg), and the mixture was hydrogenated under hydrogen at 30 psi for 2 hours. The mixture was filtered through celite, and solvent was removed from the filtrate under reduced pressure, to provide 5,6-diamino-1-ethyl-3-propyl-1,3-dihydropyrimidine-2,4-dione, a compound of formula (2).

MS m/z 213.03 ($M^+$), 235.06 ($M^+$+Na)

B. Preparation of a Compound of Formula (2) varying $R^1$ and $R^2$

Similarly, following the procedure of Example 6A, but replacing 6-amino-1-ethyl-5-nitroso-3-propyl-1,3-dihydropyrimidine-2,4-dione with other compounds of formula (1), the following compounds of formula (2) were prepared:

5,6-diamino-1-methyl-3-propyl-1,3-dihydropyrimidine-2,4-dione;

5,6-diamino-1-methyl-3-cyclopropylmethyl-1,3-dihydropyrimidine-2,4-dione;

5,6-diamino-1-ethyl-3-cyclopropylmethyl-1,3-dihydropyrimidine-2,4-dione;

5,6-amino-1-methyl-3-(2-methylpropyl)-1,3-dihydropyrimidine-2,4-dione; and 5,6-diamino-1-ethyl-3-(2-methylpropyl)-1,3-dihydropyrimidine-2,4-dione.

C. Preparation of a Compound of Formula (2) varying $R^1$ and $R^2$

Similarly, following the procedure of Example 6A, but replacing 6-amino-1-ethyl-5-nitroso-3-propyl-1,3-dihydropyrimidine-2,4-dione with other compounds of formula (1), other compounds of formula (2) are prepared.

EXAMPLE 7

Preparation of a Compound of Formula (3)

A. Preparation of a Compound of Formula (3) in which $R^1$ is n-Propyl, $R^2$ is Ethyl, X is 1,4-Pyrazolyl, Y is Methylene, and Z is 3-Trifluoromethylphenyl

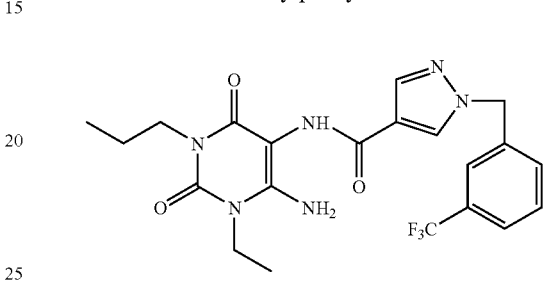

To a mixture of 5,6-diamino-1-ethyl-3-propyl-1,3-dihydropyrimidine-2,4-dione (100 mg, 0.47 mmol) and 1-{[3-(trifluoromethyl)phenyl]methyl}pyrazole-4-carboxylic acid (0.151 g, 0.56 mmol) in methanol (10 ml) was added 1-(3-dimethylaminopropyl)-3-ethylcarbodiimide hydrochloride (0.135 g, 0.7 mmol), and the reaction mixture was stirred overnight at room temperature. The solvent was removed under reduced pressure, and the residue purified using Bistag, eluting with 10% methanol/methylene chloride, to provide N-(6-amino-1-ethyl-2,4-dioxo-3-propyl(1,3-dihydropyrimidin-5-yl))(1-{[3-(trifluoromethyl)phenyl]methyl}-pyrazol-4-yl)carboxamide.

$^1$H-NMR (DMSO-d6) δ 8.59 (s, 1H), 8.02 (s, 1H), 7.59–7.71 (m, 4H), 6.71 (s, 2H), 5.51 (s, 2H), 3.91–3.96 (m, 2H), 3.70–3.75 (m, 2H), 1.47–1.55 (m, 2H), 1.14 (t, 3H, J=7.03 Hz), 0.85 (t, 3H, J=7.42 Hz).

B. Preparation of a Compound of Formula (3), varying $R^1$, $R^2$, X, Y, and Z

Similarly, following the procedure of Example 7A or 7B, but optionally replacing 5,6-diamino-1-ethyl-3-propyl-1,3-dihydropyrimidine-2,4-dione with other compounds of formula (2), and optionally replacing 1-{[3-(trifluoromethyl)phenyl]methyl}pyrazole-4-carboxylic acid with other compounds of formula Z-Y—X—CO$_2$H, the following compounds of formula (3) were prepared:

N-(6-amino-1-methyl-2,4-dioxo-3-propyl(1,3-dihydropyrimidin-5-yl))(1-{[3-(trifluoromethyl)phenyl]methyl}-pyrazol-4-yl)carboxamide;

N-(6-amino-1-methyl-2,4-dioxo-3-cyclopropylmethyl(1,3-dihydropyrimidin-5-yl))(1-{[3-(trifluoromethyl)phenyl]methyl}-pyrazol-4-yl)carboxamide;

N-(6-amino-1-ethyl-2,4-dioxo-3-cyclopropylmethyl(1,3-dihydropyrimidin-5-yl))(1-{[3-(trifluoromethyl)phenyl]methyl}-pyrazol-4-yl)carboxamide;

N-(6-amino-1-methyl-2,4-dioxo-3-ethyl(1,3-dihydropyrimidin-5-yl))(1-{[3-fluorophenyl]methyl}-pyrazol-4-yl)carboxamide;

N-(6-amino-1-methyl-2,4-dioxo-3-cyclopropylmethyl(1,3-dihydropyrimidin-5-yl))(1-{[3-fluorophenyl]methyl}-pyrazol-4-yl)carboxamide;

N-(6-amino-1-ethyl-2,4-dioxo-3-cyclopropylmethyl(1,3-dihydropyrimidin-5-yl))(1-{[3-fluorophenyl]methyl}-pyrazol-4-yl)carboxamide;

N-[6-amino-3-(cyclopropylmethyl)-1-methyl-2,4-dioxo(1,3-dihydropyrimidin-5-yl)][1-benzylpyrazol-4-yl]carboxamide;

N-(6-amino-1-methyl-2,4-dioxo-3-cyclopropylmethyl(1,3-dihydropyrimidin-5-yl))(1-{[3-cyanophenyl]methyl}-pyrazol-4-yl)carboxamide;

[1-(2-(1H-1,2,3,4-tetraazol-5-yl)ethyl)pyrazol-4-yl]-N-[6-amino-3-(cyclopropylmethyl)-1-methyl-2,4-dioxo(1,3-dihydropyrimidin-5-yl)]carboxamide;

N-[6-amino-3-(cyclopropylmethyl)-1-ethyl-2,4-dioxo(1,3-dihydropyrimidin-5-yl)](1-{[6-(trifluoromethyl)(3-pyridyl)]methyl}pyrazol-4-yl)carboxamide;

N-[6-amino-3-propyl)-1-ethyl-2,4-dioxo(1,3-dihydropyrimidin-5-yl)](1-{(2-pyridyl)]methyl}pyrazol-4-yl)carboxamide;

N-[6-amino-3-(2-methylpropyl)-1-methyl-2,4-dioxo(1,3-dihydropyrimidin-5-yl)][1-benzylpyrazol-4-yl]carboxamide;

N-[6-amino-3-(2-methylpropyl)-1-methyl-2,4-dioxo(1,3-dihydropyrimidin-5-yl)][1-{[3-fluorophenyl]methyl}pyrazol-4-yl]carboxamide;

N-[6-amino-3-(2-methylpropyl)-1-ethyl-2,4-dioxo(1,3-dihydropyrimidin-5-yl)][1-{[3-fluorophenyl]methyl}pyrazol-4-yl]carboxamide;

N-[6-amino-3-(2-methylpropyl)-1-methyl-2,4-dioxo(1,3-dihydropyrimidin-5-yl)][1-{[3-(trifluoromethyl)phenyl]methyl}pyrazol-4-yl]carboxamide; and N-[6-amino-3-(2-methylpropyl)-1-ethyl-2,4-dioxo(1,3-dihydropyrimidin-5-yl)](1-{[6-(trifluoromethyl)(3-pyridyl)]methyl}pyrazol-4-yl)carboxamide.

C. Preparation of a Compound of Formula (2) varying $R^1$ and $R^2$

Similarly, following the procedure of Example 7A, but optionally replacing 5,6-diamino-1-ethyl-3-propyl-1,3-dihydropyrimidine-2,4-dione with other compounds of formula (2), and optionally replacing 1-{[3-(trifluoromethyl)phenyl]methyl}pyrazole-4-carboxylic acid with other compounds of formula Z-Y—X—CO$_2$H, other compounds of formula (3) are prepared.

EXAMPLE 8

Preparation of a Compound of Formula I

A. Preparation of a Compound of Formula I in which $R^1$ is n-Propyl, $R^2$ is Ethel, X is 1,4-Pyrazolyl, Y is Methylene, and Z is 3-Trifluoromethylphenyl

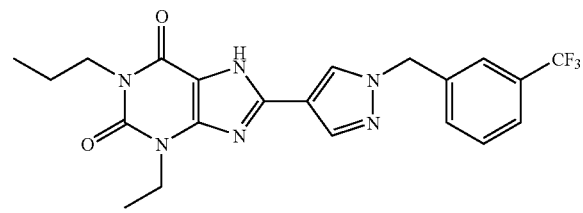

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (80 mg, 0.17 mmol), 10% aqueous sodium hydroxide (5 ml), and methanol (5 ml) was stirred at 100° C. for 2 hours. The mixture was cooled, methanol removed under reduced pressure, and the residue diluted with water and acidified with hydrochloric acid. The precipitate was filtered off, washed with water, then methanol, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60–7.75 (m, 4H), 5.54 (s, 2H), 4.05–4.50 (m, 2H), 3.87–3.91 (m, 2H), 1.55–1.64 (m, 2H), 1.25 (t, 3H, J=7.03 Hz), 0.90 (t, 3H, J=7.42 Hz); MS m/z 447.2 (M$^+$).

B. Preparation of a Compound of Formula I, varying $R^1$, $R^2$, X, Y, and Z

Similarly, following the procedure of Example 8A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (3), the following compounds of Formula I were prepared:

1-cyclopropylmethyl-3-methyl-8-[1-(phenylmethyl)pyrazol-4-yl]-1,3,7-trihydropurine-2,6-dione;

1-cyclopropylmethyl-3-methyl-8-{1-[(3-trifluoromethylphenyl)methyl]pyrazol-4-yl}-1,3,7-trihydropurine-2,6-dione;

1-cyclopropylmethyl-3-ethyl-8-{1-[(3-trifluoromethylphenyl)methyl]pyrazol-4-yl}-1,3,7-trihydropurine-2,6-dione;

1-cyclopropylmethyl-3-methyl-8-{1-[(3-fluorophenyl)methyl]pyrazol-4-yl}-1,3,7-trihydropurine-2,6-dione;

1-cyclopropylmethyl-3-ethyl-8-{1-[(3-fluorophenyl)methyl]pyrazol-4-yl}-1,3,7-trihydropurine-2,6-dione;

1-cyclopropylmethyl-3-ethyl-8-(1-{[6-(trifluoromethyl)(3-pyridyl)]methyl}pyrazol-4-yl)-1,3,7-trihydropurine-2,6-dione;

3-({4-[1-(cyclopropylmethyl)-3-methyl-2,6-dioxo-1,3,7-trihydropurin-8-yl]pyrazolyl}methyl)benzenecarbonitrile;

8-[1-(2-(1H-1,2,3,4-tetraazol-5-yl)ethyl)pyrazol-4-yl]-3-methyl-1-cyclopropylmethyl-1,3,7-trihydropurine-2,6-dione;

1-(2-methylpropyl)-3-methyl-8-[1-benzylpyrazol-4-yl]-1,3,7-trihydropurine-2,6-dione;

1-(2-methylpropyl)-3-ethyl-8-{1-[(3-fluorophenyl)methyl]pyrazol-4-yl}-1,3,7-trihydropurine-2,6-dione;

1-(2-methylpropyl)-3-methyl-8-{1-[(3-trifluoromethylphenyl)methyl]pyrazol-4-yl}-1,3,7-trihydropurine-2,6-dione;

1-(2-methylpropyl)-3-methyl-8-{1-[(3-fluorophenyl)methyl]pyrazol-4-yl}-1,3,7-trihydropurine-2,6-dione;

3-ethyl-1-(2-methylpropyl)-8-(1-{[6-(trifluoromethyl)(3-pyridyl)]methyl}pyrazol-4-yl)-1,3,7-trihydropurine-2,6-dione;

1-ethyl-3-methyl-8-{1-[(3-fluorophenyl)methyl]pyrazol-4-yl}-1,3,7-trihydropurine-2,6-dione; and 3-ethyl-1-propyl-8-[1-(2-pyridylmethyl)pyrazol-4-yl]-1,3,7-trihydropurine-2,6-dione.

C. Preparation of a Compound of Formula I, varying $R^1$, $R^2$, X, Y, and Z

Similarly, following the procedure of Example 8A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (3), other compounds of Formula I are prepared.

EXAMPLE 9

Preparation of a Compound of Formula (10)

A. Preparation of a Compound of Formula (10) in which $R^1$ is n-Propyl

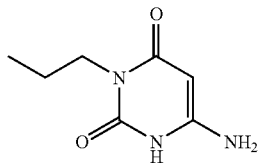

A mixture of 6-aminouracil (5.08 g, 40 mmol), hexamethyldisilazane (50 ml), and ammonium sulfate (260 mg, 1.96 mmol) was refluxed for 12 hours. After cooling, the solid was filtered off, and solvent was removed from the filtrate under reduced pressure to provide the trimethylsilylated derivative of 6-aminouracil.

The product was dissolved in toluene (1.5 ml), and iodopropane (7.8 ml, 80 mmol) and heated in an oil bath at 120° C. for 2 hours. The reaction mixture was then cooled to 0° C., and saturated aqueous sodium bicarbonate added slowly. The resulting precipitate was filtered off, and washed sequentially with water, toluene, and ether, to provide 6-amino-3-propyl-1,3-dihydropyrimidine-2,4-dione, a compound of formula (10), which was used in the next reaction with no further purification.

$^1$H-NMR (DMSO-d6) δ 10.34 (s, 1H), 6.16 (s, 2H), 4.54 (s, 1H), 3.57–3.62 (m, 2H), 1.41–1.51 (m, 2H), 0.80 (t, 3H, J=7.43 Hz).

B. Preparation of a Compound of Formula (10) varying $R^1$

Similarly, following the procedure of Example 9A, but replacing iodopropane with other alkyl halides of formula $R^1$Hal, other compounds of formula (10) are prepared, including:
6-amino-3-cyclopropylmethyl-1,3-dihydropyrimidine-2,4-dione; and
6-amino-3-(2-methylpropyl)-1,3-dihydropyrimidine-2,4-dione.

EXAMPLE 10

Preparation of a Compound of Formula (11)

A. Preparation of a Compound of Formula (10) in which $R^1$ is n-Propyl

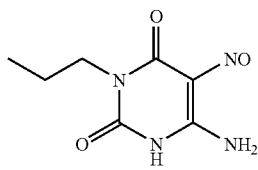

To a solution of 6-amino-3-propyl-1,3-dihydropyrimidine-2,4-dione (5.6 g) in a mixture of 50% acetic acid/water (160 ml) at 70° C. was added sodium nitrite (4.5 g) in portions over a period of 15 minutes. The mixture was stirred at 70° C. for 45 minutes, then the reaction mixture concentrated to a low volume under reduced pressure. The solid was filtered off, and washed with water, to provide 6-amino-5-nitroso-3-propyl-1,3-dihydropyrimidine-2,4-dione, a compound of formula (11).

$^1$H-NMR (DMSO-d6) δ 11.42 (s, 1H), 7.98 (s, 1H), 3.77–3.81 (m, 2H), 3.33 (s, 1H), 1.55–1.64 (m, 2H), 0.89 (t, 3H, J=7.43 Hz); MS m/z 198.78 (M$^+$), 220.78 (M++Na)

B. Preparation of a Compound of Formula (11), varying $R^1$

Similarly, following the procedure of Example 10A, but replacing 6-amino-3-propyl-1,3-dihydropyrimidine-2,4-dione with other compounds of formula (10), other compounds of formula (11) are prepared, including:
6-amino-5-nitroso-3-cyclopropylmethyl-1,3-dihydropyrimidine-2,4-dione; and
6-amino-5-nitroso-3-(2-methylpropyl)-1,3-dihydropyrimidine-2,4-dione.

EXAMPLE 11

Preparation of a Compound of Formula (12)

A. Preparation of a Compound of Formula (12) in which $R^1$ is n-Propyl

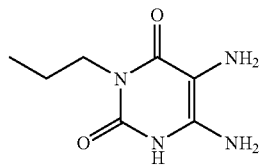

To a solution of 6-amino-5-nitroso-3-propyl-1,3-dihydropyrimidine-2,4-dione (5.4 g, 27 mmol) in 12.5% aqueous ammonia (135 ml) at 70° C. was added sodium dithionite (Na$_2$S$_2$O$_4$, 9.45 g, 54 mmol) in portions over 15 minutes, and the mixture was stirred for 20 minutes. The solution was concentrated under reduced pressure, cooled to 5° C., the precipitate filtered off, and washed with cold water, to provide 5,6-diamino-3-propyl-1,3-dihydropyrimidine-2,4-dione, a compound of formula (12).

$^1$H-NMR (DMSO-d6) δ 0.81 (t, 3H, J=7.43 Hz), 1.43–1.52 (m, 2H), 3.63–3.67 (m, 2H), 5.56 (s, 2H); MS m/z 184.95 (M$^+$), 206.96 (M$^+$+Na)

B. Preparation of a Compound of Formula (12), varying $R^1$

Similarly, following the procedure of Example 11A, but replacing 6-amino-3-propyl-1,3-dihydropyrimidine-2,4-dione with other compounds of formula (11), other compounds of formula (12) are prepared, including:
5,6-diamino-3-cyclopropylmethyl-1,3-dihydropyrimidine-2,4-dione; and
5,6-diamino-3-(2-methylpropyl)-1,3-dihydropyrimidine-2,4-dione.

EXAMPLE 12

Preparation of a Compound of Formula (13)

A. Preparation of a Compound of Formula (13) in which $R^1$ is n-Propyl, X is 1,4-Pyrazolyl, Y is Methylene, and Z is 3-Trifluoromethylphenyl

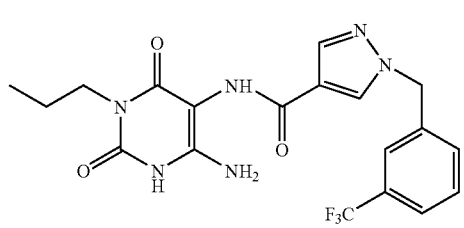

To a mixture of 5,6-diamino-3-propyl-1,3-dihydropyrimidine-2,4-dione (2.3 g, 126 mmol) and 1-{[3-(trifluoromethyl)phenyl]methyl}pyrazole-4-carboxylic acid (3.79 g, 14 mmol) in methanol (50 ml) was added 1-(3-dimethylaminopropyl)-3-ethylcarbodiimide hydrochloride (2.67 g, 14 mmol), and the reaction mixture was stirred for 3 days at room temperature (although less time is acceptable). The precipitate was filtered off, and was washed sequentially with water, and methanol. The product was dried under vacuum to provide N-(6-amino-2,4-dioxo-3-propyl(1,3-dihydropyrimidin-5-yl))(1-{[3-(trifluoromethyl)phenyl]methyl}pyrazol-4-yl)carboxamide, a compound of formula (13).

$^1$H-NMR (DMSO-d6) δ 10.44 (s, 1H), 8.56 (s, 1H), 8.37 (s, 1H), 8.00 (s, 1H), 7.56–7.71 (m, 3H), 6.02 (s, 1H), 5.49 (s, 2H), 3.62–3.66 (m, 2H), 1.44–1.53 (m, 2H), 0.82 (t, 3H, J=7.43 Hz); MS m/z 458.92 (M$^+$+Na).

B. Alternative Preparation of a Compound of Formula (3) in which R$^1$ is n-Propyl, X is 1,4-Pyrazolyl, Y is Methylene, and Z is 3-Trifluoromethylphenyl A solution of 1-{[3-(trifluoromethyl)phenyl]methyl}pyrazole-4-carboxylic acid (1 g, 3.7 mmol) in thionyl chloride (1 ml) was heated at 70° C. for 4 hours. Excess thionyl chloride was distilled off, and the residue treated with methylene chloride/hexanes. The solvent was removed under reduced pressure, and the residue dissolved in acetonitrile. This solution was added to a suspension of 5,6-diamino-3-propyl-1,3-dihydropyrimidine-2,4-dione (2.3 g, 126 mmol) and triethylamine (1 ml) in acetonitrile (20 ml) at 0° C., and stirred for 16 hours. The reaction mixture was quenched with water (5 ml), acidified with hydrochloric acid, stirred for 30 minutes, and the precipitate filtered off. The product was washed with ether, to provide N-(6-amino-2,4-dioxo-3-propyl(1,3-dihydropyrimidin-5-yl))(1-{[3-(trifluoromethyl)phenyl]methyl}pyrazol-4-yl)carboxamide, a compound of formula (13).

C. Preparation of a Compound of Formula (13), varying R$^1$, X, Y, and Z

Similarly, following the procedure of Example 12A or 12B, but optionally replacing 6-amino-3-propyl-1,3-dihydropyrimidine-2,4-dione with other compounds of formula (12), and optionally replacing 1-{[3-(trifluoromethyl)phenyl]methyl}pyrazole-4-carboxylic acid with other compounds of formula Z-Y—X—CO$_2$H, other compounds of formula (13) are prepared, including:

N-(6-amino-2,4-dioxo-3-cyclopropylmethyl(1,3-dihydropyrimidin-5-yl))(1-{[3-(trifluoromethyl)phenyl]methyl}pyrazol-4-yl)carboxamide;

N-(6-amino-2,4-dioxo-3-(2-methylpropyl)(1,3-dihydropyrimidin-5-yl))(1-{[3-(trifluoromethyl)phenyl]methyl}pyrazol-4-yl)carboxamide;

N-(6-amino-2,4-dioxo-3-propyl(1,3-dihydropyrimidin-5-yl))(1-{[3-fluorophenyl]methyl}pyrazol-4-yl)carboxamide;

N-(6-amino-2,4-dioxo-3-cyclopropylmethyl(1,3-dihydropyrimidin-5-yl))(1-{[3-fluorophenyl]methyl}pyrazol-4-yl)carboxamide;

N-(6-amino-2,4-dioxo-3-(2-methylpropyl)(1,3-dihydropyrimidin-5-yl))(1-{[3-fluorophenyl]methyl}pyrazol-4-yl)carboxamide;

N-(6-amino-2,4-dioxo-3-propyl(1,3-dihydropyrimidin-5-yl))(1-[1-benzyl]pyrazol-4-yl)carboxamide;

N-(6-amino-2,4-dioxo-3-cyclopropylmethyl(1,3-dihydropyrimidin-5-yl))(1-[1-benzyl]pyrazol-4-yl)carboxamide;

N-(6-amino-2,4-dioxo-3-(2-methylpropyl)(1,3-dihydropyrimidin-5-yl))(1-[1-benzyl]pyrazol-4-yl)carboxamide;

N-(6-amino-2,4-dioxo-3-propyl(1,3-dihydropyrimidin-5-yl))(1-{[3-cyanophenyl]methyl}pyrazol-4-yl)carboxamide;

N-(6-amino-2,4-dioxo-3-cyclopropylmethyl(1,3-dihydropyrimidin-5-yl))(1-{[3-cyanophenyl]methyl}pyrazol-4-yl)carboxamide;

N-(6-amino-2,4-dioxo-3-(2-methylpropyl)(1,3-dihydropyrimidin-5-yl))(1-{[3-cyanophenyl]methyl}pyrazol-4-yl)carboxamide;

N-(6-amino-2,4-dioxo-3-propyl(1,3-dihydropyrimidin-5-yl))(1-{[-(2-(1H-1,2,3,4-tetraazol-5-yl)ethyl)pyrazol-4-yl}carboxamide;

N-(6-amino-2,4-dioxo-3-cyclopropylmethyl(1,3-dihydropyrimidin-5-yl))(1-{[1-(2-(1H-1,2,3,4-tetraazol-5-yl)ethyl)pyrazol-4-yl)carboxamide;

N-(6-amino-2,4-dioxo-3-(2-methylpropyl)(1,3-dihydropyrimidin-5-yl))(1-{[1-(2-(1H-1,2,3,4-tetraazol-5-yl)ethyl)pyrazol-4-yl)carboxamide;

N-(6-amino-2,4-dioxo-3-propyl(1,3-dihydropyrimidin-5-yl))(1-{[6-(trifluoromethyl)(3-pyridyl)]methyl}pyrazol-4-yl)carboxamide;

N-(6-amino-2,4-dioxo-3-cyclopropylmethyl(1,3-dihydropyrimidin-5-yl))(1-{[6-(trifluoromethyl)(3-pyridyl)]methyl}pyrazol-4-yl)carboxamide; and N-(6-amino-2,4-dioxo-3-(2-methylpropyl)(1,3-dihydropyrimidin-5-yl))(1-{[6-(trifluoromethyl)(3-pyridyl)]methyl}pyrazol-4-yl)carboxamide.

EXAMPLE 13

Preparation of a Compound of Formula (3)

A. Preparation of a Compound of Formula (3) in which R$^1$ is n-Propyl, R$^2$ is Ethyl, X is 1,4-Pyrazolyl, Y is Methylene, and Z is 3-Trifluoromethylphenyl

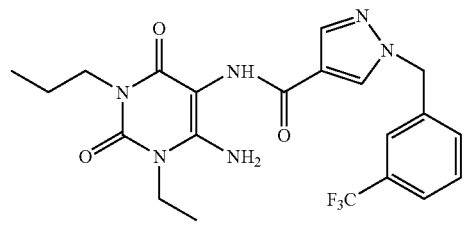

A mixture of a solution of N-(6-amino-2,4-dioxo-3-propyl(1,3-dihydropyrimidin-5-yl))(1-{[3-(trifluoromethyl)-phenyl]methyl}pyrazol-3-yl)carboxamide (872 mg, 2 mmol) in dimethylformamide (10 ml), potassium carbonate (552 mg, 4 mmol) and ethyl iodide (0.24 ml, 3 mmol) was stirred at room temperature overnight. The reaction mixture was filtered, and the solvent was evaporated from the filtrate under reduced pressure. The residue was stirred with water for two hours at room temperature, and the precipitate filtered off, washed with water, and then dissolved in methanol. The solvent was then removed under reduced pressure to provide N-(6-amino-1-ethyl-2,4-dioxo-3-propyl(1, 3-dihydropyrimidin-5-yl))(1-{[3-(trifluoromethyl)phenyl]methyl}pyrazol-4-yl)carboxamide, a compound of formula (3).

$^1$H-NMR (DMSO-d6): δ 8.58 (s, 1H), 8.39 (s, 1H), 8.01 (s, 1H), 7.72–7.50 (m, 4H), 6.71 (s, 2H), 5.51 (s, 2H), 4.0–3.82 (m, 2H), 3.77–3.65 (m, 2H), 1.60–1.50 (m, 2H), 1.13 (t, 3H, J=6.8 Hz), 0.84 (t, 3H, J=7.2 Hz); MS m/z 462.9 (M$^-$)

B. Preparation of a Compound of Formula (13), varying $R^1$, X, Y, and Z

Similarly, following the procedure of Example 13A, but replacing N-(6-amino-2,4-dioxo-3-propyl(1,3-dihydropyrimidin-5-yl))(1-{[3-(trifluoromethyl)-phenyl]methyl}pyrazol-3-yl)carboxamide with other compounds of formula (13), other compounds of formula (3) are prepared, including:

N-(6-amino-1-methyl-2,4-dioxo-3-propyl(1,3-dihydropyrimidin-5-yl))(1-{[3-(trifluoromethyl)phenyl]methyl}-pyrazol-4-yl)carboxamide;

N-(6-amino-1-methyl-2,4-dioxo-3-cyclopropylmethyl(1,3-dihydropyrimidin-5-yl))(1-{[3-(trifluoromethyl)phenyl]methyl}-pyrazol-4-yl)carboxamide;

N-(6-amino-1-ethyl-2,4-dioxo-3-cyclopropylmethyl(1,3-dihydropyrimidin-5-yl))(1-{[3-(trifluoromethyl)phenyl]methyl}-pyrazol-4-yl)carboxamide;

N-(6-amino-1-methyl-2,4-dioxo-3-ethyl(1,3-dihydropyrimidin-5-yl))(1-{[3-fluorophenyl]methyl}-pyrazol-4-yl)carboxamide;

N-(6-amino-1-methyl-2,4-dioxo-3-cyclopropylmethyl(1,3-dihydropyrimidin-5-yl))(1-{[3-fluorophenyl]methyl}-pyrazol-4-yl)carboxamide;

N-(6-amino-1-ethyl-2,4-dioxo-3-cyclopropylmethyl(1,3-dihydropyrimidin-5-yl))(1-{[3-fluorophenyl]methyl}-pyrazol-4-yl)carboxamide;

N-[6-amino-3-(cyclopropylmethyl)-1-methyl-2,4-dioxo(1,3-dihydropyrimidin-5-yl)][1-benzylpyrazol-4-yl]carboxamide;

N-(6-amino-1-methyl-2,4-dioxo-3-cyclopropylmethyl(1,3-dihydropyrimidin-5-yl))(1-{[3-cyanophenyl]methyl}-pyrazol-4-yl)carboxamide;

[1-(2-(1H-1,2,3,4-tetraazol-5-yl)ethyl)pyrazol-4-yl]-N-[6-amino-3-(cyclopropylmethyl)-1-methyl-2,4-dioxo(1,3-dihydropyrimidin-5-yl)]carboxamide;

N-[6-amino-3-(cyclopropylmethyl)-1-ethyl-2,4-dioxo(1,3-dihydropyrimidin-5-yl)](1-{[6-(trifluoromethyl)(3-pyridyl)]methyl}pyrazol-4-yl)carboxamide;

N-[6-amino-3-propyl)-1-ethyl-2,4-dioxo(1,3-dihydropyrimidin-5-yl)](1-{(2-pyridyl)]methyl}pyrazol-4-yl)carboxamide;

N-[6-amino-3-(2-methylpropyl)-1-methyl-2,4-dioxo(1,3-dihydropyrimidin-5-yl)][1-benzylpyrazol-4-yl]carboxamide;

N-[6-amino-3-(2-methylpropyl)-1-methyl-2,4-dioxo(1,3-dihydropyrimidin-5-yl)][1-{[3-fluorophenyl]methyl}pyrazol-4-yl]carboxamide;

N-[6-amino-3-(2-methylpropyl)-1-ethyl-2,4-dioxo(1,3-dihydropyrimidin-5-yl)][1-{[3-fluorophenyl]methyl}pyrazol-4-yl]carboxamide;

N-[6-amino-3-(2-methylpropyl)-1-methyl-2,4-dioxo(1,3-dihydropyrimidin-5-yl)][1-{[3-(trifluoromethyl)phenyl]methyl}pyrazol-4-yl]carboxamide; and N-[6-amino-3-(2-methylpropyl)-1-ethyl-2,4-dioxo(1,3-dihydropyrimidin-5-yl)](1-{[3-(trifluoromethyl)(3-pyridyl)]methyl}pyrazol-4-yl)carboxamide.

EXAMPLE 14

Preparation of a Compound of Formula I

A. Preparation of a Compound of Formula I in which $R^1$ is n-Propyl, $R^2$ is Ethyl, X is 1,4-Pyrazolyl, Y is Methylene and Z is 3-Trifluoromethylphenyl

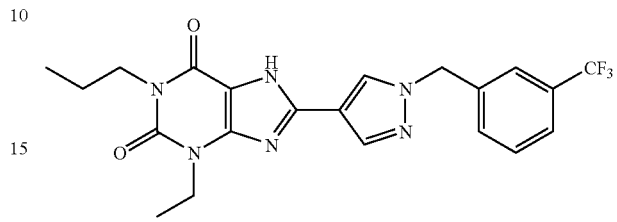

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (850 mg, 2.34 mmol), 10% aqueous sodium hydroxide (10 ml), and methanol (10 ml) was stirred at 100° C. for 18 hours. The mixture was cooled, methanol removed under reduced pressure, and the remaining mixture was acidified with hydrochloric acid to pH 2. The precipitate was filtered off, washed with water/methanol mixture, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60–7.75 (m, 4H), 5.54 (s, 2H), 4.05–4.50 (m, 2H), 3.87–3.91 (m, 2H), 1.55–1.64 (m, 2H), 1.25 (t, 3H, J=7.03 Hz), 0.90 (t, 3H, J=7.42 Hz); MS m/z 447.2 (M$^+$)

B. Preparation of a Compound of Formula I, varying $R^1$, $R^2$, X, Y, and Z

Similarly, following the procedure of Example 14A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (13), other compounds of Formula I are prepared, including those listed in Example 8.

EXAMPLE 15

Preparation of a Compound of Formula (14)

A. Preparation of a Compound of Formula (14) in which $R^2$ is Ethyl

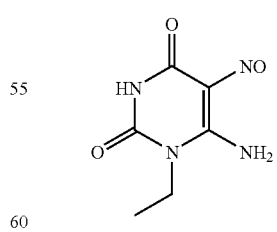

To a solution of 6-amino-1-ethyl-1,3-dihydropyrimidine-2,4-dione (5.0 g, 32.3 mmol) in a mixture of 50% acetic acid/water (50 ml) at 70° C. was added sodium nitrite (4.45 g, 64.5 mmol) in portions over a period of 30 minutes. The mixture was stirred at 70° C. for a further 30 minutes. The reaction mixture was cooled, and the precipitate filtered off, and washed with water, then methanol, to provide 6-amino-1-ethyl-5-nitroso-1,3-dihydropyrimidine-2,4-dione, a compound of formula (14).

$^1$H-NMR (DMSO-d6): δ 11.52 (s, 1H), 9.16 (s, 1H), 3.83 (q, 2H, J=7.0 Hz), 1.11 (t, 3H, J=7.0 Hz). MS m/z 184.8 (M$^+$), 206.80 (M$^+$+Na)

B. Preparation of a Compound of Formula (14), varying R$^2$

Similarly, following the procedure of Example 15A, but replacing 6-amino-1-ethyl-1,3-dihydropyrimidine-2,4-dione with 6-amino-1-methyl-1,3-dihydropyrimidine-2,4-dione, 6-amino-1-methyl-5-nitroso-1,3-dihydropyrimidine-2,4-dione was prepared.

C. Preparation of a Compound of Formula (14), varying R$^2$

Similarly, following the procedure of Example 15A, but replacing 6-amino-1-ethyl-1,3-dihydropyrimidine-2,4-dione with other compounds of formula (5), other compounds of formula (14) are prepared.

EXAMPLE 16

Preparation of a Compound of Formula (15)

A. Preparation of a Compound of Formula (15) in which R$^2$ is Ethyl

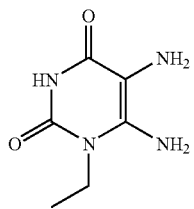

To a solution of 6-amino-1-ethyl-5-nitroso-1,3-dihydropyrimidine-2,4-dione (3.9 g, 21.2 mmol) in 14.5% aqueous ammonia (50 ml) at 50° C. was added sodium dithionite (Na$_2$S$_2$O$_4$, 7.37 g, 42.4 mmol) in portions over 15 minutes, and the mixture was stirred for 20 minutes. The solution was concentrated under reduced pressure to a volume of 30 ml, cooled to 5° C., the precipitate filtered off, and washed with cold water, to provide 5,6-diamino-1-ethyl-1,3-dihydropyrimidine-2,4-dione, a compound of formula (15).

$^1$H-NMR (DMSO-d6): δ 10.58 (s, 1H), 6.18 (s, 2H), 3.83 (q, 2H, J=7.2 Hz), 2.82 (s, 2H), 1.10 (t, 3H, J=7.2 Hz).

B. Preparation of a Compound of Formula (15), varying R$^2$

Similarly, following the procedure of Example 16A, but replacing 6-amino-1-ethyl-5-nitroso-1,3-dihydropyrimidine-2,4-dione with 6-amino-1-methyl-5-nitroso-1,3-dihydropyrimidine-2,4-dione, 5,6-diamino-1-methyl-1,3-dihydropyrimidine-2,4-dione was prepared.

C. Preparation of a Compound of Formula (15), varying R$^2$

Similarly, following the procedure of Example 16A, but replacing 6-amino-1-ethyl-5-nitroso-1,3-dihydropyrimidine-2,4-dione with other compounds of formula (14), other compounds of formula (15) are prepared.

EXAMPLE 17

Preparation of a Compound of Formula (16)

A. Preparation of a Compound of Formula (16) in which R$^2$ is Ethyl, X is 1,4-Pyrazolyl, Y is Methylene, and Z is 3-Trifluoromethylphenyl

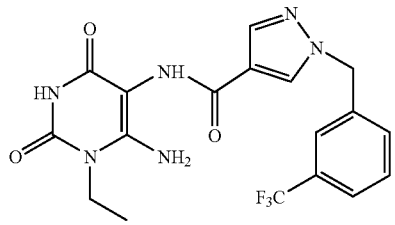

To a mixture of 5,6-diamino-1-ethyl-1,3-dihydropyrimidine-2,4-dione (2 g, 11.76 mmol) and 1-{[3-(trifluoromethyl)phenyl]methyl}pyrazole-4-carboxylic acid (3.5 g, 12.94 mmol) in methanol (50 ml) was added 1-(3-dimethylaminopropyl)-3-ethylcarbodiimide hydrochloride (2.47 g, 12.94 mmol), and the reaction mixture was stirred for 16 hours at room temperature. Solvent was removed under reduced pressure, and the residue was washed with water and methanol. The product was dried under vacuum to provide N-(6-amino-1-ethyl-2,4-dioxo(1,3-dihydropyrimidin-5-yl))(1-{[3-(trifluoromethyl)phenyl]methyl}pyrazol-4-yl)carboxamide, a compound of formula (16).

$^1$H-NMR (DMSO-d6): δ 10.60 (s, 1H), 8.50 (s, 1H), 8.39 (s, 1H), 8.01 (s, 1H), 7.72–7.50 (m, 4H), 6.69 (s, 2H), 5.50 (s, 2H), 3.87 (q, 2H, J=7.2 Hz), 1.11 (t, 3H, 7.2 Hz); MS m/z 421 (M$^-$)

B. Preparation of a Compound of Formula (16), varying R$^2$, X, Y, and Z

Similarly, following the procedure of Example 17A, but replacing 5,6-diamino-1-ethyl-1,3-dihydropyrimidine-2,4-dione with 5,6-diamino-1-methyl-1,3-dihydropyrimidine-2,4-dione, N-(6-amino-1-methyl-2,4-dioxo(1,3-dihydropyrimidin-5-yl))(1-{[3-(trifluoromethyl)phenyl]methyl}pyrazol-4-yl)carboxamide was prepared.

C. Preparation of a Compound of Formula (16), varying R$^2$, X, Y, and Z

Similarly, following the procedure of Example 16A, but replacing 5,6-diamino-1-ethyl-1,3-dihydropyrimidine-2,4-dione with other compounds of formula (14), other compounds of formula (15) are prepared.

EXAMPLE 18

Preparation of a Compound of Formula (3)

A. Preparation of a Compound of Formula (3) in which R$^1$ is n-Propyl, R$^2$ is Ethyl, X is 1,4-Pyrazolyl, Y is Methylene, and Z is 3-Trifluoromethylphenyl

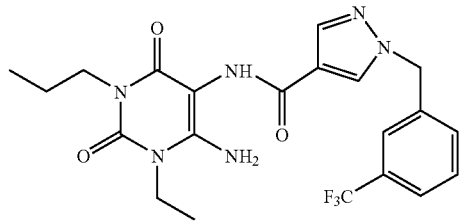

A mixture of a solution of N-(6-amino-1-ethyl-2,4-dioxo (1,3-dihydropyrimidin-5-yl))(1-{[3-(trifluoromethyl)phenyl]methyl}pyrazol-3-yl)carboxamide (1.5 g, 3.55 mmol) in dimethylformamide (30 ml), potassium carbonate (980 mg, 7.1 mmol) and propyl iodide (724 mg, 4.26 mmol) was stirred at room temperature overnight. Water was added, and the precipitate filtered off, to provide N-(6-amino-1-ethyl-2,4-dioxo-3-propyl(1,3-dihydropyrimidin-5-yl))(1-{[3-(trifluoromethyl)phenyl]methyl}pyrazol-4-yl)carboxamide, a compound of formula (3), which was used in the next reaction with no further purification.

$^1$H-NMR (DMSO-d6): δ 8.58 (s, 1H), 8.39 (s, 1H), 8.01 (s, 1H), 7.72–7.50 (m, 4H), 6.71 (s, 2H), 5.51 (s, 2H), 4.0–3.82 (m, 2H), 3.77–3.65 (m, 2H), 1.60–1.50 (m, 2H), 1.13 (t, 3H, J=6.8 Hz), 0.84 (t, 3H, J=7.2 Hz); MS m/z 462.9 (M$^-$)

B. Preparation of a Compound of Formula (3), varying $R^1$, $R^2$, X, Y, and Z

Similarly, following the procedure of Example 18A, but replacing N-(6-amino-1-ethyl-2,4-dioxo(1,3-dihydropyrimidin-5-yl))(1-{[3-(trifluoromethyl)phenyl]-methyl}pyrazol-3-yl)carboxamide with N-(6-amino-1-methyl-2,4-dioxo(1,3-dihydropyrimidin-5-yl)), N-(6-amino-1-methyl-2,4-dioxo-3-propyl(1,3-dihydropyrimidin-5-yl))(1-{[3-(trifluoromethyl)phenyl]methyl}pyrazol-4-yl) carboxamide was prepared.

C. Preparation of a Compound of Formula (3), varying $R^1$, $R^2$, X, Y, and Z

Similarly, following the procedure of Example 18A, but optionally replacing N-(6-amino-1-ethyl-2,4-dioxo(1,3-dihydropyrimidin-5-yl))(1-{[3-(trifluoromethyl)phenyl]methyl}pyrazol-3-yl)carboxamide with other compounds of formula (15), and optionally replacing propyl iodide with other compounds of formula $R^1$Hal, other compounds of formula (3) are prepared.

EXAMPLE 19

Preparation of a Compound of Formula I

A. Preparation of a Compound of Formula I in which $R^1$ is n-Propyl, $R^2$ is Ethyl, X is 1,4-Pyrazolyl, Y is Methylene, and Z is 3-Trifluoromethylphenyl

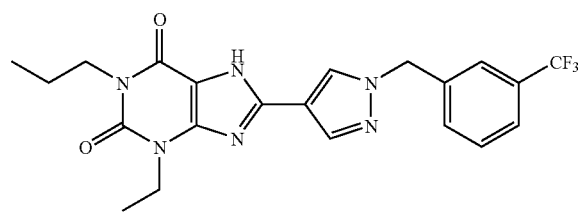

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (300 mg, 464 mmol), 20% aqueous sodium hydroxide (5 ml), and methanol (10 ml) was stirred at 80° C. for 3 hours. The mixture was cooled, methanol removed under reduced pressure, and the remaining mixture was acidified with hydrochloric acid to pH 2. The precipitate was filtered off, washed with water and methanol, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60–7.75 (m, 4H), 5.54 (s, 2H), 4.05–4.50 (m, 2H), 3.87–3.91 (m, 2H), 1.55–1.64 (m, 2H), 1.25 (t, 3H, J=7.03 Hz), 0.90 (t, 3H, J=7.42 Hz); MS m/z 447.2 (M$^+$)

EXAMPLE 20

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 21

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 22

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 23

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 24

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 25

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 26

A subcutaneous formulation may be prepared as follows:

| Ingredient | Quantity |
| --- | --- |
| Active Ingredient | 5.0 mg |
| Corn Oil | 1.0 mL |

EXAMPLE 27

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 28

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 29

Sustained Release Composition

| Ingredient | Weight Range (%) | Preferred Range (%) | Most Preferred |
| --- | --- | --- | --- |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 30

$A_{2B}$ Adenosine Receptor Assays

Methods

Radioligand binding for $A_{2B}$ adenosine receptor. Human $A_{2B}$ adenosine receptor cDNA was stably transfected into HEK-293 cells (referred to as HEK-A2B cells). Monolayer of HEK-A2B cells were washed with PBS once and harvested in a buffer containing 10 mM HEPES (pH 7.4), 10 mM EDTA and protease inhibitors. These cells were homogenized in polytron for 1 minute at setting 4 and centrifuged at 29000 g for 15 minutes at 4° C. The cell pellets were washed once with a buffer containing 10 mM HEPES (pH7.4), 1 mM EDTA and protease inhibitors, and were resuspended in the same buffer supplemented with 10% sucrose. Frozen aliquots were kept at −80° C. Competition assays were started by mixing 10 nM $^3$H-ZM241385 (Tocris Cookson) with various concentrations of test compounds and 50 µg membrane proteins in TE buffer (50 mM Tris and 1 mM EDTA) supplemented with 1 Unit/mL adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 10 µM ZM241385. The affinities of compounds (i.e. Ki values) were calculated using GraphPad software.

Radioligand binding for other adenosine receptors. Human $A_1$, $A_{2A}$, $A_3$ adenosine receptor cDNAs were stably transfected into either CHO or HEK-293 cells (referred to as CHO-A1 HEK-$A_{2A}$, CHO-A3). Membranes were prepared from these cells using the same protocol as described above. Competition assays were started by mixing 0.5 nM $^3$H- CPX (for CHO-A1), 2 nM $^3$H-ZM241385 (HEK-$A_{2A}$) or 0.1 nM $^{125}$I-AB-MECA (CHO-A3) with various concentrations of test compounds and the perspective membranes in TE buffer (50 mM Tris and 1 mM EDTA fo CHO-A1 and HEK-$A_{2A}$) or TEM buffer (50 mM Tris, 1 mM EDTA and 10 mM MgCl$_2$ for CHO-A3) supplemented with 1 Unit/mL adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 1 µM CPX (CHO-A1), 1 µM ZM214385 (HEK-$A_{2A}$) and 1 µM IB-MECA (CHO-A3). The affinities of compounds (i.e. Ki values) were calculated using GraphPad software.

cAMP measurements. Monolayer of transfected cells were collected in PBS containing 5 mM EDTA. Cells were washed once with DMEM and resuspended in DMEM containing 1 Unit/mL adenosine deaminase at a density of 100,000–500,000 cells/ml. 100 µl of the cell suspension was mixed with 25 µl containing various agonists and/or antagonists and the reaction was kept at 37° C. for 15 minutes. At the end of 15 minutes, 125 µl 0.2N HCl was added to stop the reaction. Cells were centrifuged for 10 minutes at 1000 rpm. 100 µl of the supernatant was removed and acetylated. The concentrations of cAMP in the supernatants were measured using the direct cAMP assay from Assay Design.

$A_{2A}$ and $A_{2B}$ adenosine receptors are coupled to Gs proteins and thus agonists for $A_{2A}$ adenosine receptor (such as CGS21680) or for $A_{2B}$ adenosine receptor (such as NECA) increase the cAMP accumulations whereas the antagonists to these receptors prevent the increase in cAMP accumulations-induced by the agonists. $A_1$ and $A_3$ adenosine receptors are coupled to Gi proteins and thus agonists for $A_1$ adenosine receptor (such as CPA) or for $A_3$ adenosine receptor (such as IB-MECA) inhibit the increase in cAMP accumulations-induced by forskolin. Antagonists to $A_1$ and $A_3$ receptors prevent the inhibition in cAMP accumulations.

The compounds of the invention were shown to be $A_{2B}$-antagonists by the above tests.

Compounds of the invention were also tested in a mouse model for asthma, using the procedures disclosed in U.S. Pat. No. 6,387,913, the relevant portion of which is hereby incorporated by reference, and shown to be efficacious.

What is claimed is:

1. A process for the preparation of a compound of Formula I:

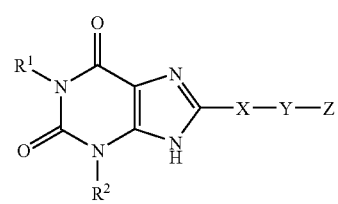

Formula I wherein:

$R^1$ and $R^2$ are independently optionally substituted alkyl;

X is pyrazol-4-yl;

Y is a covalent bond or lower alkylene; and

Z is optionally substituted monocyclic aryl or optionally substituted monocyclic heteroaryl;

comprising;
cyclizing a compound of the formula (3):

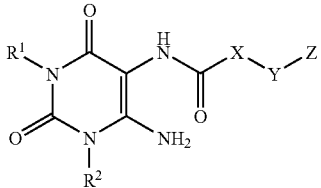
(3)

wherein $R^1$, $R^2$, X, Y, and Z are as defined above.

2. The process of claim 1, wherein the compound of formula (3) is cyclized in an inert solvent in the presence of a base.

3. The process of claim 2, wherein the inert solvent is methanol and the base is aqueous sodium hydroxide solution.

4. The process of claim 3, wherein $R^1$ and $R^2$ are independently lower alkyl, Y is methylene, and Z is optionally substituted phenyl.

5. The process of claim 4, wherein $R^1$ is n-propyl, $R^2$ is ethyl, and Z is 3-trifluoromethylphenyl.

6. The process of claim 1, wherein the compound of formula (3):

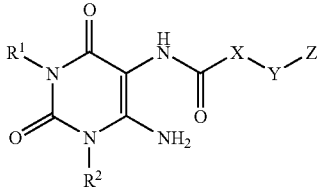
(3)

is prepared by a method comprising contacting a compound of the formula (2);

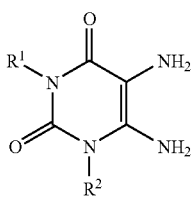
(2)

with a compound of the formula Z-Y—X—$CO_2$H in the presence of a carbodiimide or with a compound of the formula Z-Y—X—C(O)Hal, where Hal is chloro or bromo.

7. The process of claim 6, wherein the compound of formula (3) is reacted with a compound of the formula Z-Y—X—$CO_2$H in methanol.

8. The process of claim 7, wherein the carbodiimide is 1-(3)-dimethylaminopropyl-3-ethylcarbodiimide.

9. The process of claim 6, wherein the compound of formula (3) is reacted with a compound of the formula Z-Y—X—C(O)Cl.

10. The process of claim 9, wherein the reaction is carried out in an inert solvent in the presence of a tertiary base.

11. The process of claim 10, wherein the inert solvent is acetonitrile and the tertiary base is triethylamine.

12. The process of claim 6, wherein $R^1$ and $R^2$ are independently lower alkyl, X is pyrazol-4-yl, Y is methylene, and Z is optionally substituted phenyl.

13. The process of claim 12, wherein $R^1$ is n-propyl, $R^2$ is ethyl, and Z is 3-trifluoromethylphenyl, namely 3-ethyl-1-propyl-8-{1-[(3-trifluoromethylphenyl)methyl]pyrazol-4yl}-1,3,7-trihydropurine-2,6-dione.

14. The process of claim 1, wherein the compound of the formula:

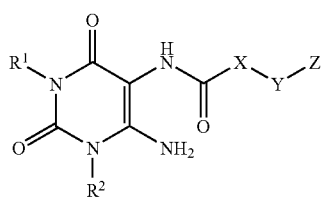
(3)

is prepared by a method comprising contacting a compound of the formula;

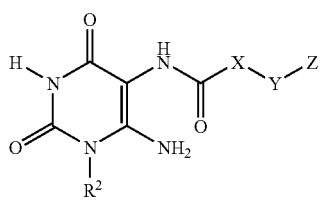
(16)

with a compound of the formula $R^1$L, in which L is a leaving group.

15. The process of claim 14, wherein $R^1$ is lower alkyl optionally substituted by cycloalkyl, and L is iodo.

16. The process of claim 15, wherein the reaction is carried out in the presence of a base in an inert solvent.

17. The process of claim 16, wherein to base is potassium carbonate and the inert solvent is N,N-dimethylformamide.

18. The process of claim 17, wherein $R^1$ and $R^2$ are independently lower alkyl, X is pyrazol-4-yl, Y is methylene, and Z is optionally substituted phenyl.

19. The process of claim 18, wherein $R^1$ is n-propyl, $R^2$ is ethyl, and Z is 3-trifluoromethylphenyl.

20. The process of claim 1, wherein the compound of the formula:

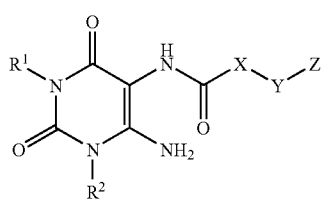
(3)

is prepared by a method comprising contacting a compound of the formula;

(13)
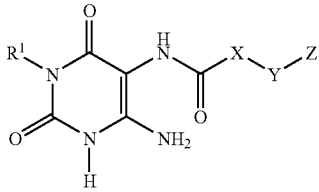

with a compound of the formula R²L, in which L is a leaving group.

21. The process of claim 20, wherein R² is lower alkyl optionally substituted by cycloalkyl, and L is iodo.

22. The process of claim 21, wherein the reaction is carried out in the presence of a base in an inert solvent.

23. The process of claim 22, wherein the base is potassium carbonate and the inert solvent is N,N-dimethylformamide.

24. The process of claim 23, wherein R¹ and R² are independently lower alkyl, X is pyrazol-4-yl, Y is methylene, and Z is optionally substituted phenyl.

25. The process of claim 24, wherein R¹ is n-propyl, R² is ethyl, and Z is 3-trifluoromethylphenyl.

26. The process of claim 14, wherein the compound of the formula:

(16)
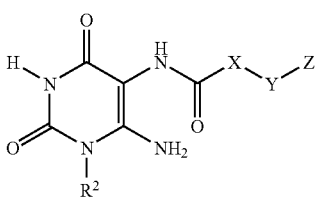

is prepared by a method comprising contacting a compound of the formula:

(15)
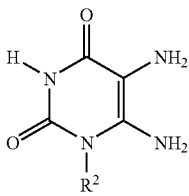

with a compound of the formula Z-Y—X—CO₂H in the presence of a carbodiimide or with a compound of the formula Z-Y—X—C(O)Hal, where Hal is chloro or bromo.

27. The process of claim 26, wherein the compound of formula (15) is reacted with a compound of the formula Z-Y—X—CO₂H in methanol.

28. The process of claim 27, wherein the carbodiimide is 1-(3-dimethylaminopropyl)-3-ethylcarbodiimide.

29. The process of claim 26, wherein the compound of formula (15) is reacted with a compound of the formula Z-Y—X—C(O)Cl.

30. The process of claim 29, wherein the reaction is carried out in an inert solvent in the presence of a tertiary base.

31. The process of claim 30, wherein the inert solvent is acetonitrile and the tertiary base is triethylamine.

32. The process of claim 31, wherein R¹ and R² are independently lower alkyl, X is pyrazol-4-yl, Y is methylene, and Z is optionally substituted phenyl.

33. The process of claim 32, wherein R¹ is n-propyl, R² is ethyl, and Z is 3-trifluoromethylphenyl.

34. The process of claim 19, wherein the compound of the formula:

(13)
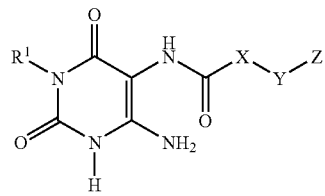

is prepared by a method comprising contacting a compound of the formula:

(12)
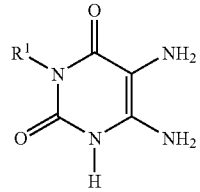

with a compound of the formula Z-Y—X—CO₂H in the presence of a carbodiimide or a compound of the formula Z-Y—X—C(O)Hal, where Hal is chloro or bromo.

35. The process of claim 34, wherein the compound of formula (12) is reacted with a compound of the formula Z-Y—X—CO₂H in methanol.

36. The process of claim 35, wherein the carbodiimide is 1-(3-dimethylaminopropy)-3-ethylcarbodiimide.

37. The process of claim 34, wherein the compound of formula (12) is reacted with a compound of the formula Z-Y—X—C(O)Cl.

38. The process of claim 37, wherein the reaction is carried out in an inert solvent in the presence of a tertiary base.

39. The process of claim 38, wherein the inert solvent is acetonitrile and the tertiary base is triethylamine.

40. The process of claim 39, wherein R¹ and R² are independently lower alkyl, X is pyrazol-4-yl, Y is methylene, and Z is optionally substituted phenyl.

41. The process of claim 40, wherein R¹ is n-propyl, R² is ethyl, and Z is 3-trifluoromethylphenyl.

42. The process of claim 34, wherein the compound of the formula:

(12)
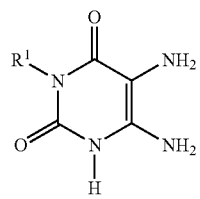

is prepared by a method comprising the steps of:
   a) contacting a compound of the formula:

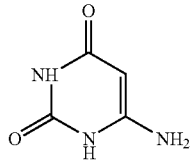

with hexamethyldisilazane in the presence of an acid catalyst;
   b) contacting the product thus formed with R¹L, where L is a leaving group, followed by;
   c) contacting the product thus formed:

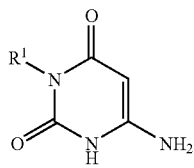
(10)

with a mixture of sodium nitrite in acetic acid/water; and
   d) contacting the product thus formed:

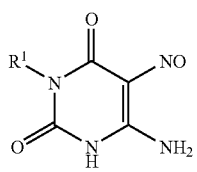
(11)

with a mixture of aqueous ammonia and sodium dithionite.

43. The process of claim 42, wherein in step a) R¹ is lower alkyl, L is iodo, and the acid catalyst is ammonium sulfate.

44. The process of claim 26, wherein the compound of the formula;

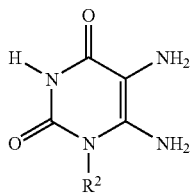
(15)

is prepared by a method comprising the steps of:
   a) contacting a compound of the formula:

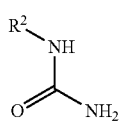

with ethyl cyanoacetate in the presence of a base in a protic solvent;
   b) contacting the product thus formed:

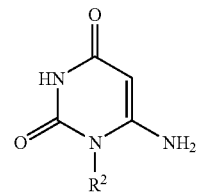

with a mixture of sodium nitrite in acetic acid/water; and
   c) contacting the product thus formed:

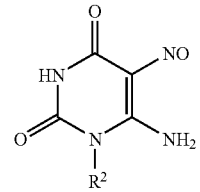

with a mixture of aqueous ammonia and sodium dithionite.

45. The process of claim 44, wherein the base is sodium ethoxide and the protic solvent is ethanol.

46. The process of claim 6, wherein the compound of formula:

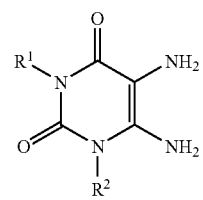
(2)

is prepared by a method comprising the steps of:
   a) contacting a compound of the formula:

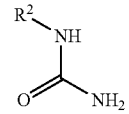
(4)

with ethyl cyanoacetate in the presence of a base in a protic solvent;
   b) contacting the product thus formed:

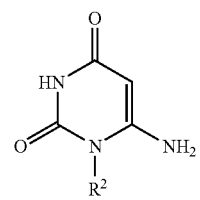

with the dimethylacetal of N,N-dimethylformamide;

c) contacting the product thus formed:

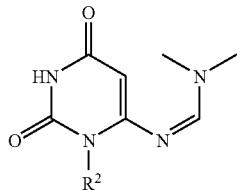

with a compound of formula R¹L, in which L is a leaving group;

d) contacting the product thus formed:

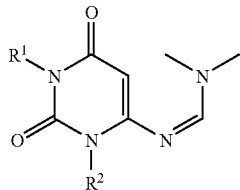

with aqueous ammonia;

e) contacting the product thus formed:

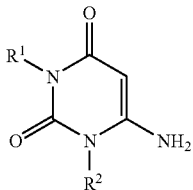

with a mixture of sodium nitrite in acetic acid/water; and f) contacting the product thus formed:

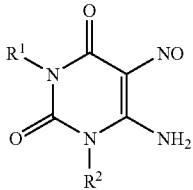

with a mixture of aqueous ammonia and sodium dithionite.

47. The process of claim 46, wherein the base is sodium ethoxide and the protic solvent is ethanol.

* * * * *

UNITED STATES PATENT AND TRADEMARK OFFICE
CERTIFICATE OF CORRECTION

PATENT NO. : 7,125,993 B2  Page 1 of 1
APPLICATION NO. : 10/719102
DATED : October 24, 2006
INVENTOR(S) : Jeff Zablocki et al.

It is certified that error appears in the above-identified patent and that said Letters Patent is hereby corrected as shown below:

In Column 55, Claim 7, line 61, "formula (3)" should read --formula (2)--

In Column 55, Claim 9, line 66, "formula (3)" should read --formula (2)--

Signed and Sealed this
Fourteenth Day of February, 2012

David J. Kappos
*Director of the United States Patent and Trademark Office*